United States Patent
Huang et al.

(10) Patent No.: US 11,399,713 B2
(45) Date of Patent: **\*Aug. 2, 2022**

(54) MEASUREMENT OF MULTI-LAYER STRUCTURES

(71) Applicants: University of Rochester, Rochester, NY (US); The University of Arizona, Tucson, AZ (US)

(72) Inventors: Jinxin Huang, Rochester, NY (US); Jannick P. Rolland, Pittsford, NY (US); Eric Clarkson, Tucson, AZ (US); Matthew Kupinski, Tucson, AZ (US)

(73) Assignees: University of Rochester, Rochester, NY (US); The University of Arizona, Tucson, AZ (US)

( * ) Notice: Subject to any disclaimer, the term of this patent is extended or adjusted under 35 U.S.C. 154(b) by 257 days.

This patent is subject to a terminal disclaimer.

(21) Appl. No.: 16/398,611

(22) Filed: Apr. 30, 2019

(65) Prior Publication Data

US 2019/0254516 A1 Aug. 22, 2019

Related U.S. Application Data

(63) Continuation-in-part of application No. 15/461,893, filed on Mar. 17, 2017, now abandoned, which is a continuation of application No. 14/548,067, filed on Nov. 19, 2014, now Pat. No. 9,615,735.

(60) Provisional application No. 61/934,201, filed on Jan. 31, 2014.

(51) Int. Cl.
*A61B 3/10* (2006.01)
*A61B 3/00* (2006.01)
*A61B 3/113* (2006.01)

(52) U.S. Cl.
CPC ............ *A61B 3/101* (2013.01); *A61B 3/0025* (2013.01); *A61B 3/102* (2013.01); *A61B 3/113* (2013.01)

(58) Field of Classification Search
CPC ......... A61B 3/101; A61B 3/102; A61B 3/113; A61B 3/0025; A61B 3/117; A61B 3/1015
See application file for complete search history.

(56) References Cited

U.S. PATENT DOCUMENTS

| | | | |
|---|---|---|---|
| 6,236,459 B1 * | 5/2001 | Negahdaripour | A61B 3/101 356/496 |
| 8,873,049 B2 | 10/2014 | Rolland et al. | |
| 9,615,735 B2 * | 4/2017 | Huang | A61B 3/101 |
| 2009/0201465 A1 | 8/2009 | Huth | |

(Continued)

OTHER PUBLICATIONS

U.S. Appl. No. 14/548,067, Final Office Action dated Sep. 16, 2016, 9 pages.

(Continued)

*Primary Examiner* — Jordan M Schwartz
(74) *Attorney, Agent, or Firm* — Kilpatrick Townsend & Stockton LLP

(57) ABSTRACT

Systems and methods for assessing multi-layer structures in which a spectrum array is generated from low coherence interferometry and input into a statistical estimator, which determines the thickness and layer number based on the inputted spectrum and other information, including information about a source intensity noise, Poisson noise, and dark noise associated with the low coherence interferometry.

8 Claims, 20 Drawing Sheets
(19 of 20 Drawing Sheet(s) Filed in Color)

(56) References Cited

U.S. PATENT DOCUMENTS

| | | | |
|---|---|---|---|
| 2011/0182517 A1* | 7/2011 | Farsiu | A61B 5/7203 |
| | | | 382/190 |
| 2012/0133887 A1 | 5/2012 | Huang | |
| 2013/0208245 A1 | 8/2013 | Campbell | |
| 2014/0016093 A1 | 1/2014 | Korb et al. | |
| 2015/0138505 A1 | 5/2015 | Grenon et al. | |
| 2015/0201829 A1* | 7/2015 | Yang | A61B 3/1025 |
| | | | 382/131 |
| 2016/0133013 A1* | 5/2016 | Docherty | G06K 9/6207 |
| | | | 382/131 |
| 2016/0338585 A1 | 11/2016 | Arieli et al. | |

OTHER PUBLICATIONS

U.S. Appl. No. 14/548,067, Non-Final Office Action dated Apr. 22, 2016, 10 pages.

U.S. Appl. No. 14/548,067, Notice of Allowance dated Dec. 7, 2016, 8 pages.

U.S. Appl. No. 14/548,067, Restriction Requirement dated Feb. 16, 2016, 9 pages.

U.S. Appl. No. 15/461,893, Final Office Action dated Feb. 27, 2019, 16 pages.

U.S. Appl. No. 15/461,893, Non-Final Office Action dated Sep. 19, 2018, 12 pages.

U.S. Appl. No. 15/461,893, Restriction Requirement dated Apr. 16, 2018, 6 pages.

Akcay et al., Effect of Source Spectral Shape on Task-Based Assessment of Detection and Resolution in Optical Coherence Tomography, Applied Optics, vol. 44, No. 35, Dec. 10, 2005, pp. 7573-7580.

Barrett et al., Statistical Decision Theory, Chapter 13, Foundations of Image Science, 2004, pp. 801-911.

Chen et al., Ultrahigh-Resolution Measurement by Optical Coherence Tomography of Dynamic Tear Film Changes on Contact Lenses, Investigative Ophthalmology & Visual Science, vol. 51, No. 4, Apr. 2010, pp. 1988-1993.

Craig et al., Refractive Index and Osmolality of Human Tears, Optometry and Vision Science, vol. 72, No. 10, Oct. 1995, pp. 718-724.

Doane, An Instrument for in Vivo Tear Film Interferometry, Optometry and Vision Science, vol. 66, No. 6, Jun. 1989, pp. 383-388.

Fogt et al., Interferometric Measurement of Tear Film Thickness by Use of Spectral Oscillations, Opt. Soc. Am. A, vol. 15, No. 1, Jan. 1998, pp. 268-275.

Huang et al., Maximum-Likelihood Estimation in Optical Coherence Tomography in the Context of the Tear Film Dynamics, Biomedical Optics Express, vol. 4, No. 10, Oct. 1, 2013, pp. 1806-1816.

Huang et al.. Phantom Study of Tear Film Dynamics with Optical Coherence Tomography and Maximum-Likelihood Estimation, Optics Letters, vol. 38, No. 10, May 15, 2013, pp. 1721-1723.

Huang et al.. Quantitative Measurement of Tear Film Dynamics with Optical Coherence Tomography and Statistical Decision Theory, Journal of Vision, vol. 12, No. 14, Article 39, Dec. 27, 2012, 1 page.

Johnson et al., Changes in the Tear Film and Ocular Surface from Dry Eye Syndrome, Progress in Retinal and Eye Research, vol. 23, 2004, pp. 449-474.

King-Smith et al., Tear Film Interferometry and Corneal Surface Roughness, Investigative Ophthalmology & Visual Science, vol. 55, No. 4, Apr. 21, 2014, pp. 2614-2618.

King-Smith et al., The Thickness of the Tear Film, Current Eye Research, vol. 29, Nos. 4-5, 2004, pp. 357-368.

Lee et al., Broadband Astigmatism-Corrected Czerny-Turner Spectrometer, Optics Express, vol. 18, No. 22, Oct. 25, 2010, pp. 23378-23384.

Lemp et al., The Definition and Classification of Dry Eye Disease, Guidelines from the 2007 International Dry Eye Workshop, the Ocular Surface, Apr. 2008, 6 pages.

Lemp et al., The Definition and Classification of Dry Eye Disease: Report of the Definition and Classification Subcommittee of the International Dry Eye Workshop, the Ocular Surface, vol. 5, No. 2, Apr. 2007, pp. 75-92.

Patel et al., Refractive Index of the Human Corneal Epithelium and Stroma, J. Refract. Surg., vol. 11, No. 2, 1994, 5 pages.

Pflugfelder et al., Management and Therapy of Dry Eye Disease: Report of the Management and Therapy Subcommittee of the International Dry Eye Workshop, The Ocular Surface, vol. 5, No. 2, Apr. 2007, 17 pages.

Prydal et al., Study of Precorneal Tear Film Thickness and Structure by Interferometry and Confocal Microscopy, Investigative Ophthalmology & Visual Science, vol. 33, No. 6, May 1992, pp. 1996-2005.

Rieger, The Importance of the Precorneal Tear Film for the Quality of Optical Imaging, British Journal of Ophthalmology, vol. 76, No. 3, Mar. 1992, pp. 157-158.

Rolland et al., Task-Based Optimization and Performance Assessment in Optical Coherence Imaging, J. Opt. Soc. Am. A, vol. 22, No. 6, Jun. 2005, pp. 1132-1142.

Schmoll et al.. Precise Thickness Measurements of Bowman's Layer, Epithelium, and Tear Film, Optometry and Vision Science, vol. 89, No. 5, May 2012, pp. E795-E802.

Tankam et al., Parallelized Multi-Graphics Processing Unit Framework for High-Speed Gabor-Domain Optical Coherence Microscopy, Journal of Biomedical Optics, vol. 19, No. 7, Jul. 2014, 11 pages.

Tiffany, Refractive Index of Meibomian and Other Lipids, Current Eye Research, vol. 5, No. 11, Nov. 1986, pp. 887-889.

Werkmeister et al.. Measurement of Tear Film Thickness Using Ultrahigh-Resolution Optical Coherence Tomography, Investigative Ophthalmology & Visual Science, vol. 54, No. 8, Aug. 15, 2013, pp. 5578-5583.

Yadav et al., Micrometer Axial Resolution OCT for Corneal Imaging, Biomedical Optics Express, vol. 2, No. 11, Nov. 1, 2011, pp. 3037-3046.

* cited by examiner

MEASUREMENT OF MULTI-LAYER STRUCTURES

CROSS-REFERENCE TO RELATED APPLICATIONS

This patent application is a continuation-in-part of U.S. patent application Ser. No. 15/461,893, filed Mar. 17, 2017, which is a continuation of U.S. patent application Ser. No. 14/548,067, filed Nov. 19, 2014, now U.S. Pat. No. 9,615,735 issued Apr. 11, 2017, which claims the benefit of U.S. provisional application No. 61/934,201, filed Jan. 31, 2014, the subject matter of each of which is incorporated in its entirety by this reference.

RELATED FIELDS

Use of low coherence interferometry, including optical coherence tomography (OCT), and statistical decision theory to assess the layers of a multi-layer structure.

BACKGROUND

There is a need for improved techniques for assessing multi-layer structures in a wide variety of arts.

In the context of tear films, Dry Eye Disease (DED) has been a serious public health issue, with symptoms including discomfort, visual disturbance, and irritation that may cause damage to the ocular surface. However, the understanding of the mechanisms underlying DED is still at an early stage. According to some, it is a prerequisite that the normal tear film be better understood if we are to advance our ability to effectively manage DED. The tear film is the ocular surface fluid that contributes to keep the cornea healthy and functional, and as such it plays a critically important role in keeping normal visual function for the ocular optical system. The normal tear film consists of three layers: the lipid layer, the aqueous layer, and the mucin layer. The lipid layer is secreted by the meibomian gland and is about 20~150 nm thick; underneath the lipid lies the aqueous layer, which contributes the largest volume to the tear and is about 3~7 microns thick; the mucin layer is the interface between the aqueous layer and the cornea, which creates a rough interface between the cornea and the aqueous layer. The rough interface serves to attach tears to the corneal surface.

Tear film instability, which is quantified as the temporal thinning of the tear film thickness leading to tear film breakup, has been established as a core mechanism of DED by some. Tear film thickness can be measured using both invasive and non-invasive methods. Since the invasive methods disturb the tear film in the measurement procedure, non-invasive methods have been sought. In 1989, Doane pioneered the development of a non-invasive interferometric method to measure the tear film (see M. G. Doane, "An instrument for in vivo tear film interferometry," Optometry Vision Sci. 66 (6), 383-388 (1989)). He used the thickness-dependent fringe method based on the principle of thin-film white light interferometry, which is known for explaining the changing colors of a soap bubble as its thickness varies. Since then, different techniques have been deployed over two decades to quantify tear film thickness: interferometry based on wavelength-dependent fringe, confocal microscopy, and spectral domain optical coherence tomography (OCT). These methods lack in their ability to provide simultaneous measurements of both the lipid and aqueous layers, or they measure at a single point and are unable to spatially quantify the tear film dynamics.

For tear film thickness measurement by spectral domain OCT, the convention is to perform a fast Fourier transform followed by a peak detection technique to extract thickness information. The axial resolution of this method is fundamentally limited by the width of the axial point spread function (PSF), which is in the order of a micron in state-of-the-art systems, thus to date OCT has been used to measure the total thickness of the lipid and aqueous layers combined.

Similar challenges exist for measurement of other types of multi-layer structures such as industrial films (e.g. coatings or tapes) and biomedical samples (e.g. skin or corneal tissue layers).

SUMMARY

We have developed systems and methods for assessing a wide variety of multi-layer structures, including tear films and multi-layer structures with repeating layers.

To extend our understanding of tear film dynamics for the management of dry eye disease, we have developed systems and methods to optically sense the tear film and estimate simultaneously the thicknesses of the lipid and aqueous layers. In one non-limiting example, SDT-OCT, combines ultra-high axial resolution optical coherence tomography (OCT) and a robust estimator based on statistical decision theory (SDT) to achieve thickness measurements at the nanometer scale. Unlike conventional Fourier-domain OCT where peak detection of layers occurs in Fourier space, in SDT-OCT thickness is estimated using statistical decision theory directly on the raw spectra acquired with the OCT system. In one non-limiting example, a customized OCT system tailored to ~1 μm axial point spread function (FWHM) in the corneal tissue, combined with a maximum-likelihood estimator, can estimate thicknesses of the nanometer-scale lipid and micron-scale aqueous layers of the tear film, simultaneously, with nanometer precision. The framework is validated in experiments using a physical phantom that consists of two layers of optical coatings that mimic the lipid and aqueous layers of the tear film.

In some non-limiting embodiments, we combine the axial selectivity capability of OCT with statistical decision theory (SDT). In this approach, SDT is applied directly to each raw spectrum acquired by the OCT system to estimate the thickness configuration that has most likely generated a given spectrum. In some instances, this SDT-OCT may be distinguished from conventional spectral domain OCT because SDT-OCT combines modeling with a hardware solution and enables thickness estimation down to nanometer scale with nanometer precision, as required for the lipid layer, a two orders of magnitude improvement from the conventional approach.

The systems and methods we have developed enable the simultaneous estimation of the thicknesses of the lipid and aqueous layers, and have developed the theoretical framework that takes into account different sources of statistical noise associated with the imaging chain. In one example, we have formulated a maximum-likelihood (ML) estimator as the observer to extract the dual thickness information. In another example, we have developed OCT hardware instrumentation as well as the experimental validation of SDT-OCT with a custom-developed physical phantom.

In addition to tear films, the systems and methods we have developed are also applicable to other multi-layer structures, including without limitation industrial films and biomedical samples.

In one example, a method of determining layer thickness of a multi-layer structure includes: (a) directing light from a light source of a low coherence interferometry (LCI) component to a multi-layer structure, the multi-layer structure including one or more stack units each stack unit having at least a first layer of a first material system on top of a second layer of a second, different material system; (b) collecting spectrally dispersed light at a detection module of the low coherence interferometry component, the collected light including back-reflected or back-scattered light from at least one of the stack units; (c) generating a spectrum array of spectral intensity values derived from the light collected at the detection module; (d) inputting the spectrum array into a statistical estimator comprising a processor and a memory; and (e) at the statistical estimator, simultaneously determining thickness estimates for the at least first and second layers of one or more stack units of the multi-layer structure based on a statistical likelihood of the inputted spectrum array being generated by the estimated layer thicknesses out of different possible combinations of layer thicknesses.

In some instances, the low coherence interferometry component may be an optical coherence tomography component.

In some instances, the statistical estimator further determines an estimate for a number of stack units in the multi-layer structure based on the inputted spectrum array.

In some instances, the one or more stack units includes a plurality of repeating stack units including: (i) a top stack unit including at least a layer of the first material and a layer of the second material, the layer of the first material of the top stack unit adjacent an incidence medium; (ii) a bottom stack unit including at least a layer of the first material and a layer of the second material, the layer of the second material of the bottom stack unit adjacent a substrate; and (iii) at least one middle stack unit including at least a layer of the first material and a layer of the second material.

In some instances, collecting light at the detector module includes collecting: (i) light reflected or scattered back from the top stack unit, (ii) light reflected or scattered back from the bottom stack unit, and (iii) light reflected or scattered back from the at least one middle stack unit.

In some instances, the statistical estimator further determines an estimate for a roughness of at least one of a top interface and a bottom interface of the repeating stack units.

In some instances, the statistical estimator determines the thickness estimates and the stack unit number estimate based on the inputted spectrum array and at least one of a light source statistical noise, Poisson noise, and dark noise of the low coherence interferometry component.

In some instances, the statistical estimator determines the thickness estimates and the stack unit number estimate based on the inputted spectrum array and a light source statistical noise, a Poisson noise, and a dark noise of the low coherence interferometry component.

In some instances, the light source is a broadband source.

In some instances, the low coherence interferometry component is a micron axial resolution low coherence interferometry component and the statistical estimator is a nanometer resolution statistical estimator.

In some instances, the low coherence interferometry component is a micron axial resolution Fourier domain optical coherence tomography component and the statistical estimator is a nanometer resolution statistical estimator.

In some instances, the Fourier domain optical coherence tomography component is a spectral domain optical coherence tomography component and the detection module is a spectrometer.

In some instances, the Fourier domain optical coherence tomography component is a swept source optical coherence tomography component and the light source is a temporally swept frequency light source.

In another example, a system for determining layer thickness of a multi-layer structure includes: (a) a low coherence interferometry component having a light source and a detection module, the low coherence interferometry component configured to: (i) direct light from a light source to the multi-layer structure, the multi-layer structure including a plurality of stack units, the stack units each including a first layer of a first material on top of a second layer of a second, different material; (ii) collect light at the detection module, the collected light including back-reflected or back-scattered light from at least some of the stack units; and (iii) generate a spectrum array based on the light collected at the detection module; and (b) a statistical estimator comprising a processor and a memory, the statistical estimator configured to simultaneously determine thickness estimates for the layers of the stack units based on a statistical likelihood of the inputted spectrum array being generated by the estimated layer thicknesses out of different possible combinations of layer thicknesses.

In some instances, the statistical estimator is configured to further determine an estimate for a number of stack units in the multi-layer structure based on the inputted spectrum array.

In some instances, the plurality of stack units includes: (i) a top stack unit including at least a layer of the first material and a layer of the second material, the layer of the first material of the top stack unit adjacent an incidence medium; (ii) a bottom stack unit including at least a layer of the first material and a layer of the second material, the layer of the second material of the bottom stack unit adjacent a substrate; and (iii) at least one middle stack unit including at least a layer of the first material and a layer of the second material.

In some instances, the detection module is configured to collect light reflected or scattered back from the top stack unit, light reflected or scattered back from the bottom stack unit, and light reflected or scattered back from the at least one middle stack unit.

In some instances, the statistical estimator is configured to further determine an estimate for a roughness of at least one of a top interface and a bottom interface of the stack units.

In some instances, the statistical estimator is configured to determine the thickness estimates and the stack unit number estimate based on the inputted spectrum array and at least one of a light source statistical noise, Poisson noise, and dark noise of the low coherence interferometry component.

In some instances, the statistical estimator is configured to determine the thickness estimates and the stack unit number estimate based on the inputted spectrum array and a light source statistical noise, a Poisson noise, and a dark noise of the low coherence interferometry component.

In some instances, the light source is a broadband source.

In some instances, the low coherence interferometry component is a micron axial resolution low coherence interferometry component and the statistical estimator is a nanometer resolution statistical estimator.

In another example, a method of determining layer thicknesses of a multi-layer film includes: (a) directing light from a light source to the multi-layer film, the multi-layer film having at least a first layer and a second layer; (b) collecting light at a detection module, the collected light including back-reflected or back-scattered light from the multi-layer film, the light source and the detection module being components of an low coherence interferometry component; (c)

generating a spectrum array based on the light collected at the detection module; (d) inputting the spectrum array into a statistical estimator including a processor and a memory; and (e) at the statistical estimator, simultaneously determining estimates of at least a first layer thickness for the first layer and a second layer thickness for the second layer based on a statistical likelihood of the inputted spectrum array being generated by the estimated first layer thickness and the estimated second layer thickness out of different possible combinations of potential first layer thicknesses and potential second layer thicknesses, wherein the statistical estimator estimates the first and second layer thicknesses based on the inputted spectrum array and at least one of a quantified intensity noise of the light source, a quantified Poisson noise of the light detector, and a quantified dark noise of the detector.

In some instances, the estimated thicknesses are determined at a nanometer scale.

In some instances, the low coherence interferometry component is a micron axial resolution low coherence interferometry component.

In some instances, the generated spectrum array includes an array with a plurality of elements in which at least some of the elements are each proportional to a number of electrons accumulated at a location on the light detector over a time segment.

In some instances, the statistical estimator estimates the thicknesses based on the inputted spectrum array, the intensity noise of the light source, the Poisson noise of the light detector, and the dark noise of the detector.

In some instances, the light source is a broadband source.

In another example, a system for determining layer thicknesses of a multi-layer film, the system includes: (a) a low coherence interferometry component configured to generate data about the multi-layer film, the low coherence interferometry component having a light source and a detector; and (b) a statistical estimator component configured to generate an estimate of a first layer thickness of the multi-layer film and an estimate of a second layer thickness of the multi-layer film based on the generated data and based on data on light source noise and detector noise.

In some instances, the low coherence interferometry component includes a light source, a beam splitter, a reference arm, a sample arm, and a detector.

In some instances, the light source is a broadband source and the detector is a spectrometer.

In some instances, the statistical estimator component generates the estimates based on the generated data, the generated data being based on a spectrum measured by the detection module.

In some instances, the statistical estimator is at least one of a maximum-likelihood estimator, a maximum posteriori estimator, or a posterior mean estimator.

In some instances, the low coherence interferometry component is a micron axial resolution low coherence intereferometry component and the statistical estimator component is a nanometer resolution statistical estimator.

In some instances, the low coherence interferometry component has an operational bandwidth of at least 200 nm.

In some instances, the low coherence interferometry component has an operational bandwidth of approximately 400 nm.

In some instances, the low coherence interferometry component operates in a spectral window including 600 nm and 1000 nm wavelengths.

In some instances, the light source noise data is a quantified intensity noise of the light source, and the detector noise data is a quantified Poisson noise of the detector and a quantified dark noise of the detector.

In some instances, the statistical estimator component determines a combination of layer thickness estimates that are most likely based on the generated data, the light source noise data, and the detector noise data.

In some instances, the statistical estimator component is configured to simultaneously generate the estimate of the layer thicknesses based on the generated data, the light source noise data, and the detector noise data.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Tear Film Measurement
1. Theoretical Framework

In one non-limiting embodiment, we address a dual estimation problem given one spectrum measurement per lateral position on the cornea. This section details one example of the mathematical modeling of SDT-OCT and the principle of ML estimation for two layers.

Figure 1:
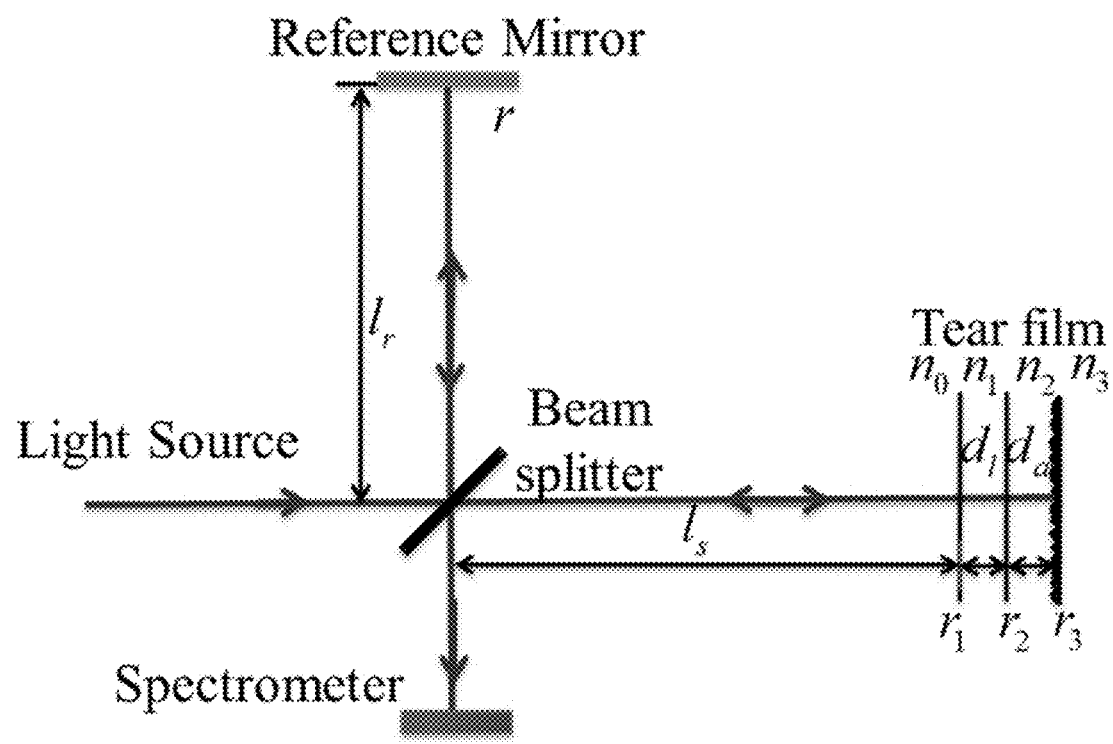
FIG. 1 is a schematic layout of a non-limiting example of spectral domain OCT in the context of tear film imaging.

1.1 Mathematical Modeling of SDT-OCT for a Two-Layer Tear Film Thickness Estimation An example of OCT system hardware tailored to this application is schematically shown in FIG. 1. In FIG. 1, the detector is a spectrometer, from which the output is a spectrum array. The broadband light source emits an electric field that can be regarded as a superposition of plane waves. The electric field for a plane wave with an angular frequency w is denoted as $E_s(\omega,t)$. It is split at the beamsplitter and propagates to both reference and sample arms. The response $m_r(\omega)$ to the electric field $E_s(\omega,t)$, due to propagation through the reference arm, can be written as $$m_r(\omega) = \frac{1}{2} r \cdot \exp\left(i 2 n_0 \frac{\omega}{c} l_r\right), \quad (1)$$

where r is the reflectance of the mirror, $n_0$ the refractive index of air, c is the velocity of light in vacuum, and $l_r$ is the length of the reference arm. This term is set to be zero when a common path configuration is used by blocking the reference arm with a beam block.

Similarly, the response $m_s(\omega)$ from the sample arm can be derived as $$m_s(\omega) = \frac{1}{2}\Big(r_1 + r_2(1-r_1^2) \cdot \exp\left(i 2 n_1 \frac{\omega}{c} d_l\right) +$$
$$r_3(1-r_1^2)(1-r_2^2) \cdot \exp\left(i 2 n_1 \frac{\omega}{c} d_l + i 2 n_2 \frac{\omega}{c} d_a\right)\Big) \cdot \left(i 2 n_0 \frac{\omega}{c} l_s\right), \quad (2)$$

where $n_1$, $n_2$, and $n_3$ denote the refractive indices of lipid, aqueous, and corneal epithelium, respectively; $d_l$ and $d_a$ are the thicknesses of the lipid and aqueous layers, respectively; $l_s$ is the length of the sample arm; and $r_1$, $r_2$, and $r_3$ denote the reflectance of the air-lipid, lipid-aqueous, and aqueous-cornea interfaces, respectively. It is worth noting that the refractive indices and the reflectance have dependence on the optical frequency due to dispersion, and this dependence is accounted for in the model. Since there is no distinct interface between the aqueous and mucin layers, we consider them as one layer in this example. Due to the microplicae and glycocalyx on the corneal surface, the interface between the tear film and the cornea is rough as illustrated in FIG. 1. The reflectance at the rough interface between the aqueous and the cornea is given as $$r_3 = \frac{n_2 - n_3}{n_2 + n_3} \cdot \exp\left(-2\sigma^2 n_2^2 \frac{\omega^2}{c^2}\right), \quad (3)$$

where σ is the standard deviation of the surface height of the aqueous-cornea interface.

The back-reflected light from both arms recombine at the beamsplitter and the resulting interference pattern is collected by the spectrometer in which a dispersive element (i.e, a grating in the case of this setup) is used to disperse the light. A high-speed line-scan camera is used to record the intensity of the modulated signal as a function of wavelength. For a given line-scan camera with M pixels, the output from the spectrometer is a discretized spectrum $N_g$, which is an array with M elements. For the $x^{th}$ pixel along the line-scan camera, the digital reading $N_g(x,\Delta t)$ is proportional to the number of electrons accumulated in that pixel sensor during the integration time $\Delta t$. Given the source intensity noise as well as the Poisson noise and dark noise of the detector, the randomness of $N_g(x,\Delta t)$ may be approximated by a normal distribution as $$N_g(x,\Delta t) \square \text{Normal}\left(\langle\langle\langle N_{g|(d_l,d_a)}(x,\Delta t)\rangle\rangle\rangle, K_{N_{g|(d_l,d_a)}}(x,\Delta t)\right), \quad (4)$$

$\langle\langle\langle N_{g|(d_l,d_a)}(x,\Delta t)\rangle\rangle\rangle$ represents the ensembles average of the output over all sources of noise, for a given lipid layer thickness $d_l$ and aqueous layer thickness $d_a$, and is given as $$\langle\langle\langle N_{g|(d_l,d_a)}(x,\Delta t)\rangle\rangle\rangle = \frac{R(x)}{e}\Delta t \int_{\omega_x - \Delta\omega_x}^{\omega_x} S(\omega)|m_r(\omega) + m_s(\omega)|^2 d\omega + N_{dark}, \quad (5)$$

where $S(\omega)$ is the power spectral density of the source, $N_{dark}$ is the average dark noise over the integration time, $\Delta\omega_x$ is the optical frequency bandwidth at the $x^{th}$ pixel, e is the charge of an electron, and $R(x)$ is the pixel's responsivity. In this example, $K_{N_g|(d_l,d_a)}$ is a M×M covariance matrix, but only the diagonal elements of the matrix are non-zero. Thus $K_{N_g|(d_l,d_a)}$ can be simplified as an M element array that denotes the variance of the readout at each pixel, and may be experimentally quantified as discussed further below.

1.2 Formulation of the Maximum-likelihood Estimator for the Lipid and Aqueous Layers In at least some instances, the OCT system is a point-to-point imaging modality. During one measurement, a spectrum $N_g$ from one lateral point of the sample is acquired. For a measured spectrum $N_g$, the likelihood of this spectrum being generated by different possible combinations of tear film thicknesses $d_l$ and $d_a$ is given as $$P(N_g \mid d_l, d_a) = \frac{1}{(2\pi)^{\frac{M}{2}} \prod_x [K_{N_g(d_l,d_a)}(x,\Delta t)]^{\frac{1}{2}}} \times \quad (6)$$
$$\exp\left[-\frac{1}{2}\sum_x \frac{(N_g(x,\Delta t) - \langle\langle\langle N_{g|(d_l,d_a)}(x,\Delta t)\rangle\rangle\rangle)^2}{K_{N_{g(d_l,d_a)}}(x,\Delta t)}\right].$$

The ML estimator makes estimates by maximizing $P(N_g|d_l,d_a)$, which is equivalent to finding the minimum of the negative conditional log-likelihood. The estimates are then given as $$(\hat{d}_l, \hat{d}_a) = \underset{d_l, d_a}{\arg\min}(-\log(P(N_g \mid d_l, d_a))). \quad (7)$$

The ML estimator is next further detailed and applied in an experimental setting.

2. Experimental Investigation 2.1 Development of a Customized OCT System

Figure 2A:
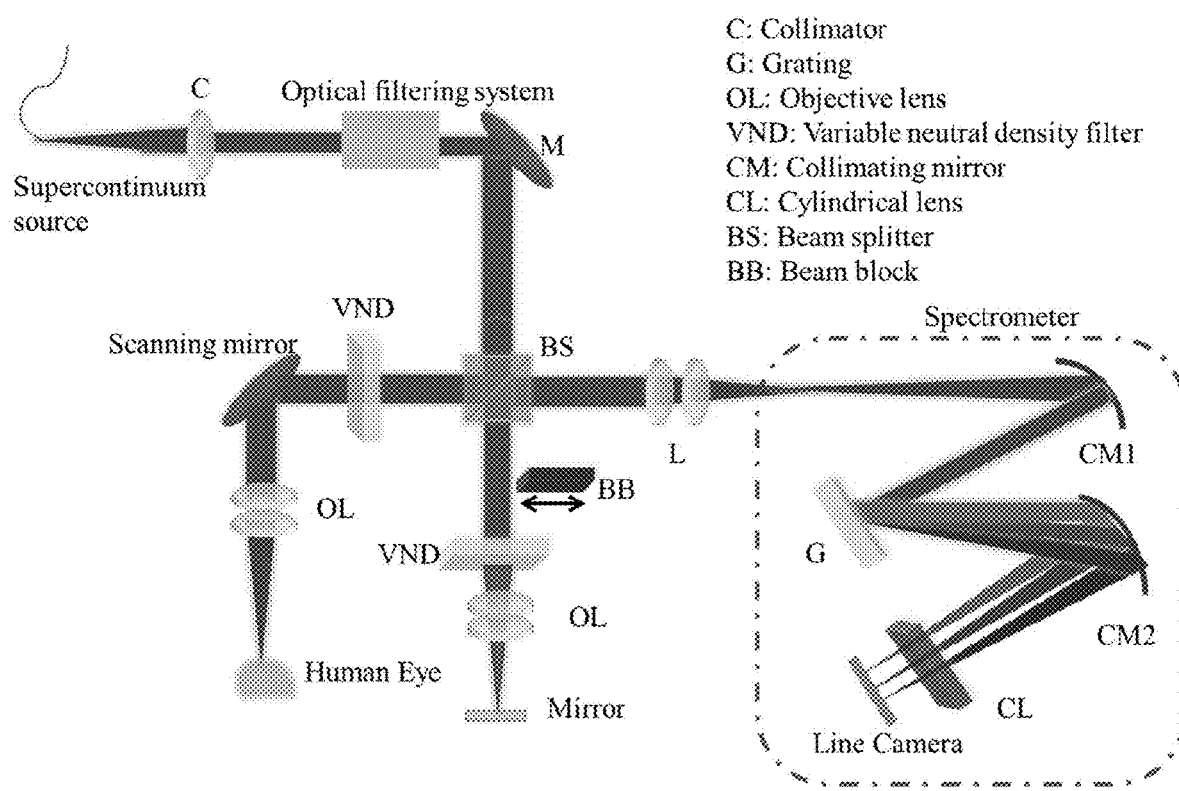
FIG. 2(a) shows a non-limiting example of a spectral domain OCT setup.
Figure 2B:
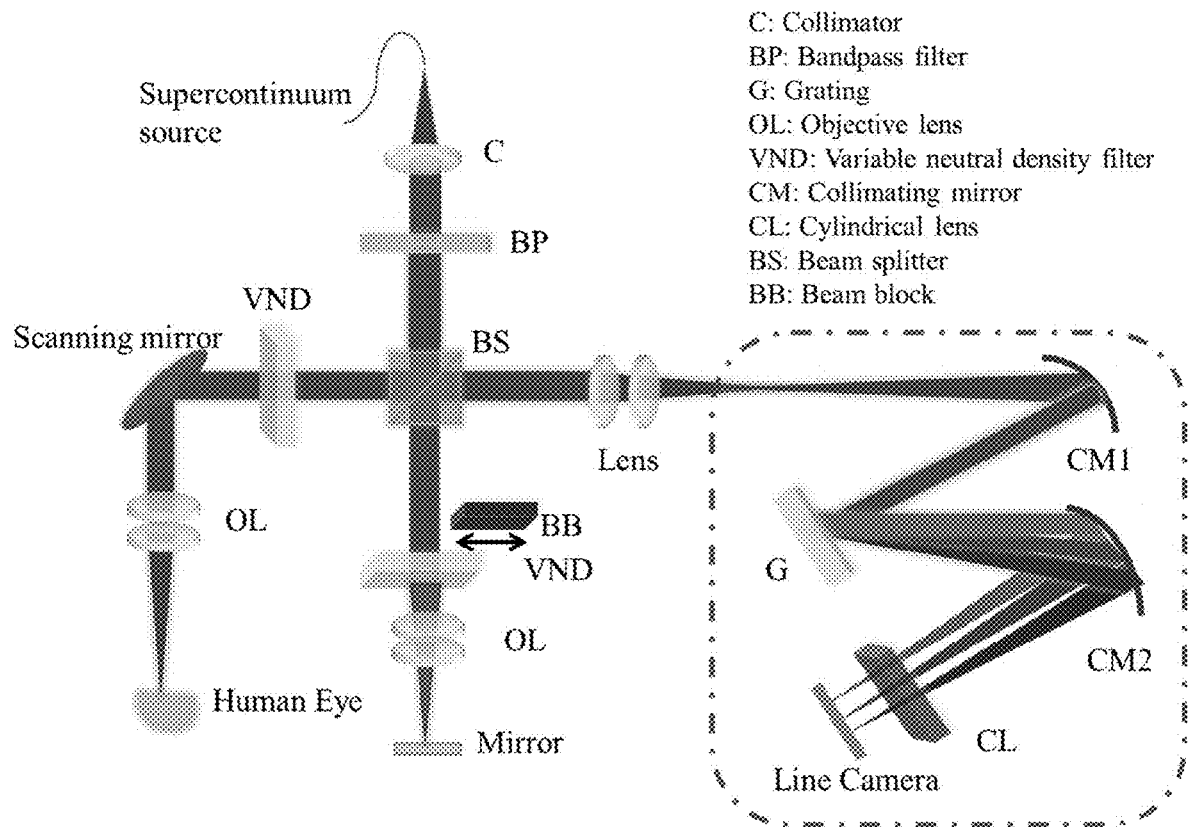
FIG. 2(b) shows another non-limiting example of a spectral domain OCT setup.
Figure 2C:
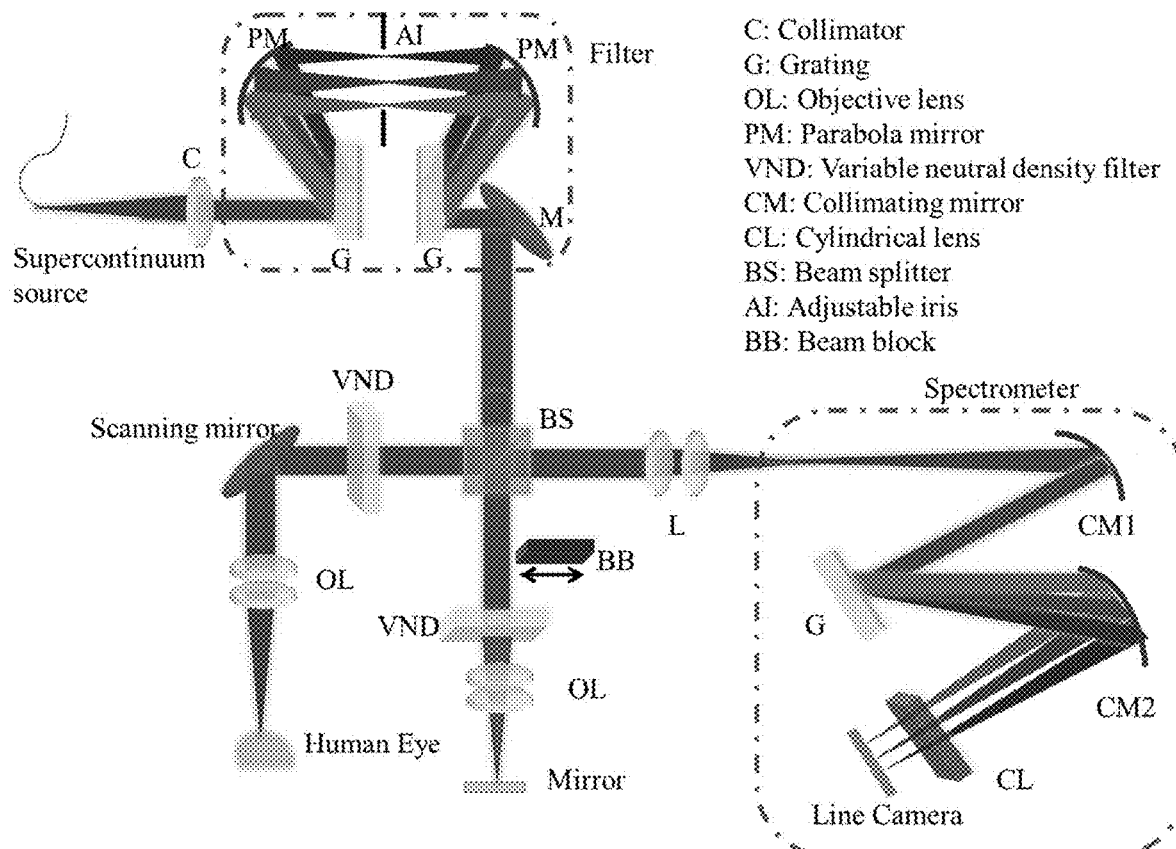
FIG. 2(c) shows another non-limiting example of a spectral domain OCT setup.

We designed and built a custom spectral-domain OCT system operating in the spectral window of 600 to 1000 nm. Because of the lack of fiber directional couplers for the considered broadband spectral window, the system was built in free-space and is schematically shown in FIG. 2(c). The OCT system consists of a commercial supercontinuum source (WhiteLase Micro, Fianium Inc.), a custom bandpass filter, and a custom broadband astigmatism-corrected Czerny-Turner spectrometer. Because no commercial filter met our requirement for this broad bandwidth, we developed an optical filter with two diffraction gratings (830 grooves/mm, Richardson Gratings™) to disperse and recombine the spectrum, two off-axis mirrors (45° off axis parabola mirror, EFL=89.28 mm, Edmund Optics Inc.), and a custom adjustable iris diaphragm to select the desired spectrum. By doing so, we eliminated the spectrum outside the operating window because it may deliver extra power to the eye and cause safety issues. In other embodiments, the custom bandpass filter of FIG. 2(c) is not necessary. In other embodiments, other optical filtering systems may be utilized (such as shown in FIGS. 2(a) and (b)). For example, in the embodiment shown in FIG. 2(b), a general bandpass filter is used for optical filtering.

After the filter, the beam is then split into a reference and a sample arms by a 50/50 non-polarizing cube beamsplitter (BS014, Thorlabs Inc.). In the sample arm, a galvanometer-based scanner (Dual axis, Cambridge Technologies Inc.) directs the beam to the sample, currently in a telecentric geometry, and is focused on the sample using a broadband NIR achromatic doublet lens (EFL=40 mm, Thorlabs Inc.). The beam size is 2 mm in diameter, yielding 20 µm FWHM lateral PSF. In the reference arm, an equivalent lens is used to compensate for the dispersion. The back reflection/scattering light beams from both arms are focused into a broadband astigmatism-corrected Czerny-Turner spectrometer. Non-limiting examples of such spectrometers are described in U.S. Pat. No. 8,873,049 for "Broad Band Czerny-Turner Spectrometer, Methods, and Applications," the entire contents of which are hereby incorporated by this reference. The spectrometer interfaced to a line-scan camera of 8192 pixels (SPL8192-70 km, Basler Inc.) provides 0.1 nm spectral resolution. In addition, the design uses a custom cylindrical lens to correct for astigmatism over the 400 nm bandwidth. In this driving application for the measurement of tear film thickness, the reference arm is used to guide the positioning of the sample at the focus of the light beam, while for imaging we block the reference arm and use the air-tear interface as a new effective reference that helps minimizing the effects of environmental vibrations as established in common path interferometers.

Any suitable computing system or group of computing systems can be used with or incorporated into the OCT systems described above. A computing system may include a processor communicatively coupled to a memory and that executes computer-executable program code and/or accesses information stored in the memory. The processor may be a microprocessor, an application-specific integrated circuit ("ASIC"), a state machine, or other processing device. The processor can include any of a number of processing devices, including one. Such a processor can include or may be in communication with a computer-readable medium storing instructions that, when executed by the processor, cause the processor to perform the desired operations. The memory may include any suitable computer-readable medium. The computer-readable medium can include any electronic, optical, magnetic, or other storage device capable of providing a processor with computer-readable instructions or other program code. Non-limiting examples of a computer-readable medium include a floppy disk, CD-ROM, DVD, magnetic disk, memory chip, ROM, RAM, an ASIC, a configured processor, optical storage, magnetic tape or other magnetic storage, or any other medium from which a computer processor can read instructions. The instructions may include processor-specific instructions generated by a compiler and/or an interpreter from code written in any suitable computer-programming language, including, for example, C, C++, C#, Visual Basic, Java, Python, Perl, JavaScript, and ActionScript. The system may also include a number of external or internal devices such as input or output devices.

In some embodiments, the system may be configured to output information concerning the thicknesses of the lipid and/or aqueous layers of a tear film. In some instances, the system is configured to output a thickness map or maps showing the thicknesses of the lipid and aqueous layers at several locations in each layer. In some instances, the system is configured to output a series of thickness maps illustrating thicknesses of the lipid and aqueous layers at different points in time. Although not shown in the figures, the OCT system may include or be used with an eye tracker to assist in compensating for natural human eye saccades in processing the final thickness map(s) (e.g. by recording lateral eye motion during imaging in order to register individual scans to one another).

2.2 Evaluation of System Parameters

In this section, certain system parameters, including the axial PSF and the statistical noise associated with the example of a customized OCT described above, are evaluated.

2.2.1 Axial Point Spread Function (PSF)

Figure 3:
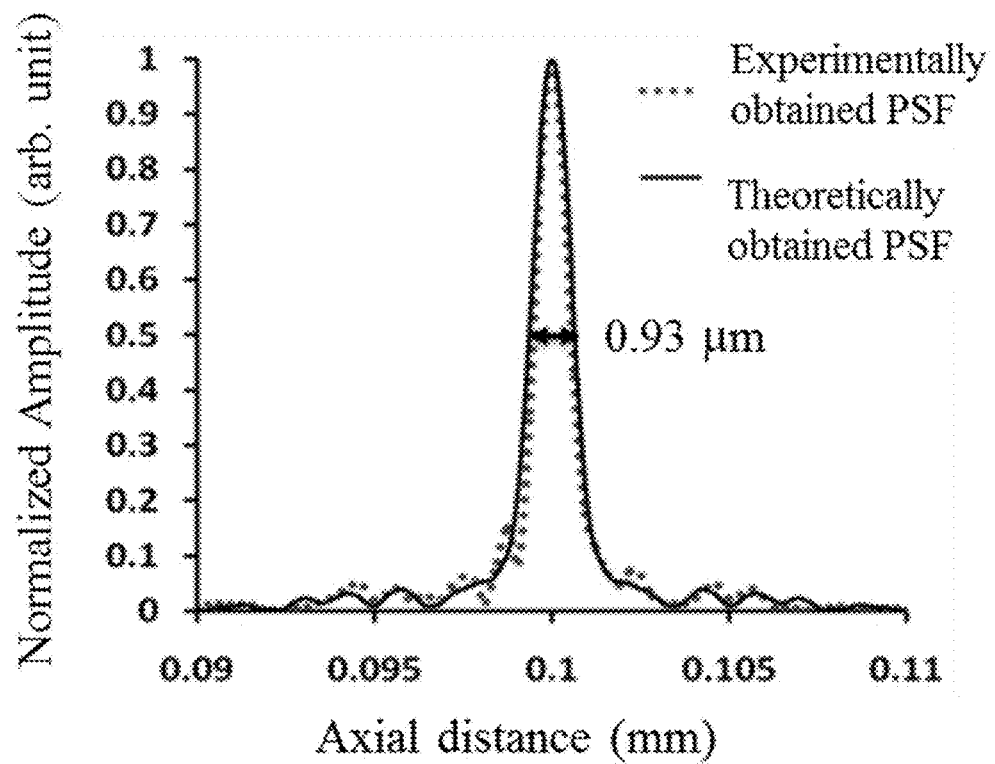
FIG. 3 shows experimental and theoretical PSF's of the OCT setup of FIG. 2(c).

The axial PSF was measured by using a flat mirror as the sample. The measured PSF width (FWHM) was calculated from the Fourier transform of the interference fringes, which was 1.30 µm in air and 0.93 µm in corneal epithelium (n=1.401). To make sure there was no PSF degradation due to k-space interpolation and dispersion, the theoretical PSF was calculated from the Fourier transform of the envelope of the interference signal, which is shown as the solid line in FIG. 3. Results show a good agreement in the evaluation of the PSF and the achievement of <1 µm axial PSF that may be helpful for at least some instances of this application. In some embodiments, an axial PSF of <2 µm may be helpful for at least some instances of this application. In some embodiments, an axial PSF of between 0.75 µm and 1.25 µm may be helpful for at least some instances of this application.

2.2.2 Characterization of System Noise

Figure 4A:
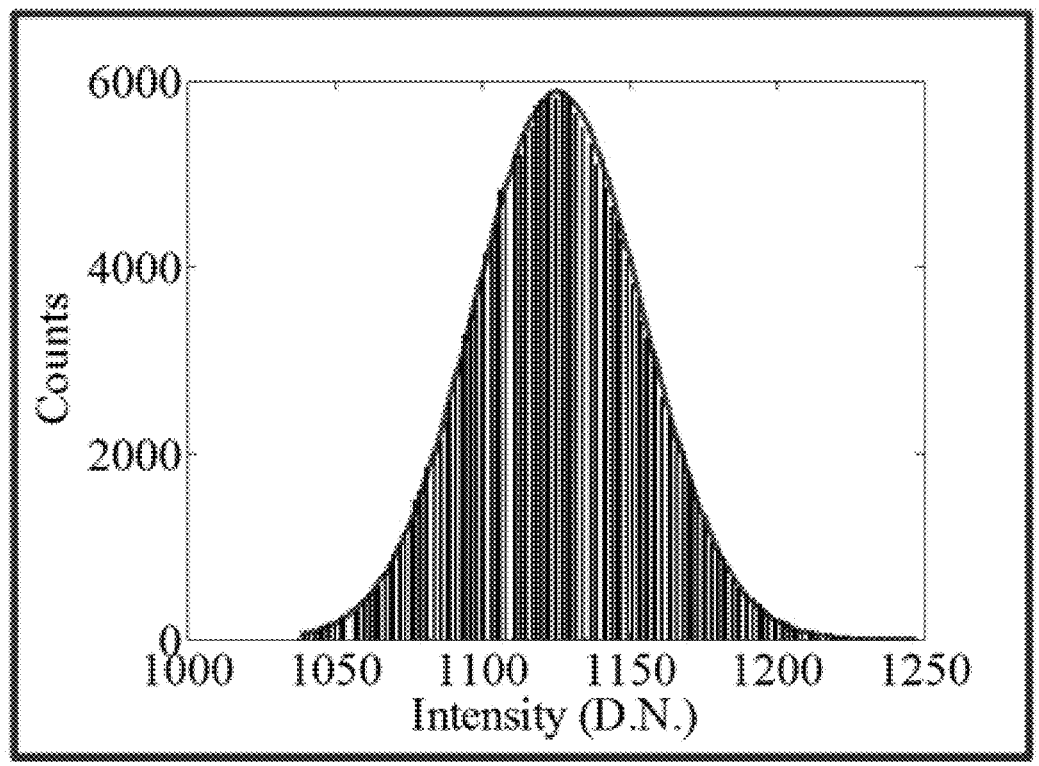
FIG. 4(a) is a histogram of camera readings at one pixel (the outer envelope is a Gaussian curve with the mean and standard deviations of the counts distribution).
Figure 4B:
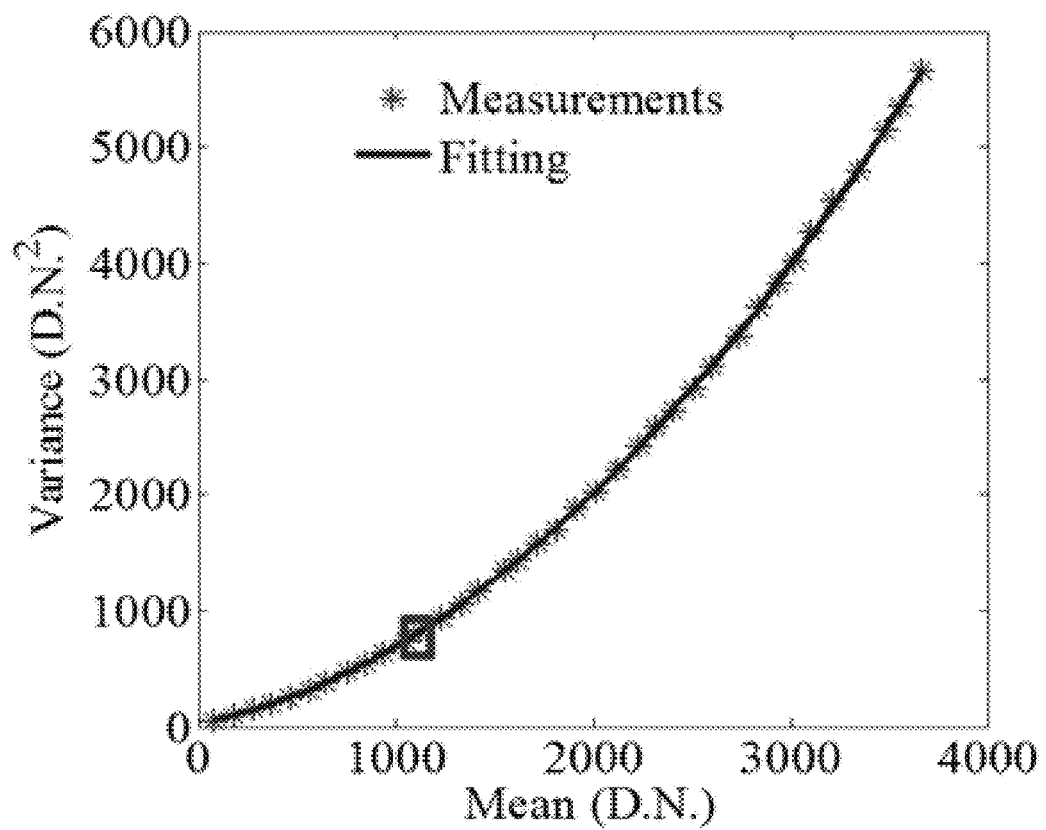
FIG. 4(b) graphically illustrates a relation between the output variance of the power spectrum and the mean value (D.N.: digital number), with the data point in the square being derived from the measurements shown in FIG. 4(a).

Since the specific variance of the output depends on the source and detector being used, in at least some instances, the variance associated with the example of the customized spectral domain OCT described above was evaluated. To quantify the variance of $N_g$, we placed a variable neutral density filter (VNDF) before the input of the spectrometer. Because all the pixels in the line-scan camera use the same type of sensor (in this particular example), the noise was evaluated at one random pixel. Readings from that chosen pixel were recorded for a fixed light intensity level. FIG. 4(a) shows the histogram of output readings, from which the mean and variance of the digital number (D.N.) were calculated. The outer envelope in FIG. 4(a) shows a Gaussian curve with the calculated mean and variance, which validates that the output follows a normal distribution. The calculated mean and variance from FIG. 4(a) correspond to the data point in the square shown in FIG. 4(b). Then as we adjusted the position of the VNDF, the intensity of the light reaching the line-scan camera monotonically increased. After quantifying the mean and the corresponding variance at different light intensity levels, the relation of the mean power spectrum value $<<<N_g(x,\Delta t)>>>$ and its variance $K_{N_g}(x,\Delta t)$ is shown in FIG. 4(b). The continuous curve in FIG. 4(b) is a second-order polynomial fitting, which gives the following relation $$K_{Ng}(x,\Delta t) = C_1 \left\langle\left\langle\left\langle N_g(x,\Delta t)\right\rangle\right\rangle\right\rangle^2 C_2$$
$$\left\langle\left\langle\left\langle N_g(x,\Delta t)\right\rangle\right\rangle\right\rangle + C_3. \quad (8)$$

From the fitting curve, the coefficients $C_1$, $C_2$, $C_3$ were evaluated to be $3.2\times10^{-4}$, 0.33, and 25, which correspond to the laser intensity noise, the Poisson noise, and the dark noise, respectively.

2.3 Phantom Preparation

To test the performance of the ML estimator described above in an experimental setup, we fabricated a physical phantom with known thicknesses that provide ground truth in the estimation task. Optical coating was chosen to make accurate deposition of a layered structure.

We deposited coatings using Ta2O5 and SiO2 on a BaK2 glass substrate, to mimic the lipid layer, the aqueous layer, and the corneal epithelium, respectively. The substrate was 3 mm thick (i.e, 4.6 mm in optical thickness) and the back surface of the substrate was grinded to be rough in order to, together with being a thick substrate, effectively eliminate any contribution from that surface. The refractive indices of these materials and the tear film components are listed in Table 1. Although the refractive indices are listed at 589 nm for comparison, the dispersion curves (the wavelength dependence of the refractive indices) of the materials were measured during manufacturing and those of the tear film components are known from the literature. The impact of the uncertainty in the refractive indices will be discussed in section 3.

The difference in refractive index between Ta2O5 and SiO2 was slightly higher than between the lipid and the aqueous layers, yet it was a best match among choices of materials that mimic the lipid and aqueous layers, and it is representative. The coating of SiO2 on top of BaK2 is a good match in refractive index difference to that of the aqueous layer on the corneal layer. Conservative uncertainties of the two layer thicknesses were within 2% of the thicknesses set by the manufacturing process. The thicknesses were measured at the coating facility with a Perkin Elmer Lambda 1050 thickness measurement unit. Ground truth was provided to be 67.3±1.3 nm and 1015.6±20.3 nm, for the lipid layer and the aqueous layer phantoms, respectively.

TABLE 1

Refreactive Indices

| Material | Refractive index (@589 nm) |
|---|---|
| Lipid | 1.4820 ± 0.0004 |
| Aqueous | 1.3371 ± 0.0015 |
| Corneal epithelium | 1.401 ± 0.005 |
| Ta2O5 | 2.11211 ± 0.00005 |
| SiO2 | 1.46964 ± 0.00005 |
| BaK2 | 1.53989 ± 0.00005 |

2.4 Validation at a Single Point

Figure 5A:
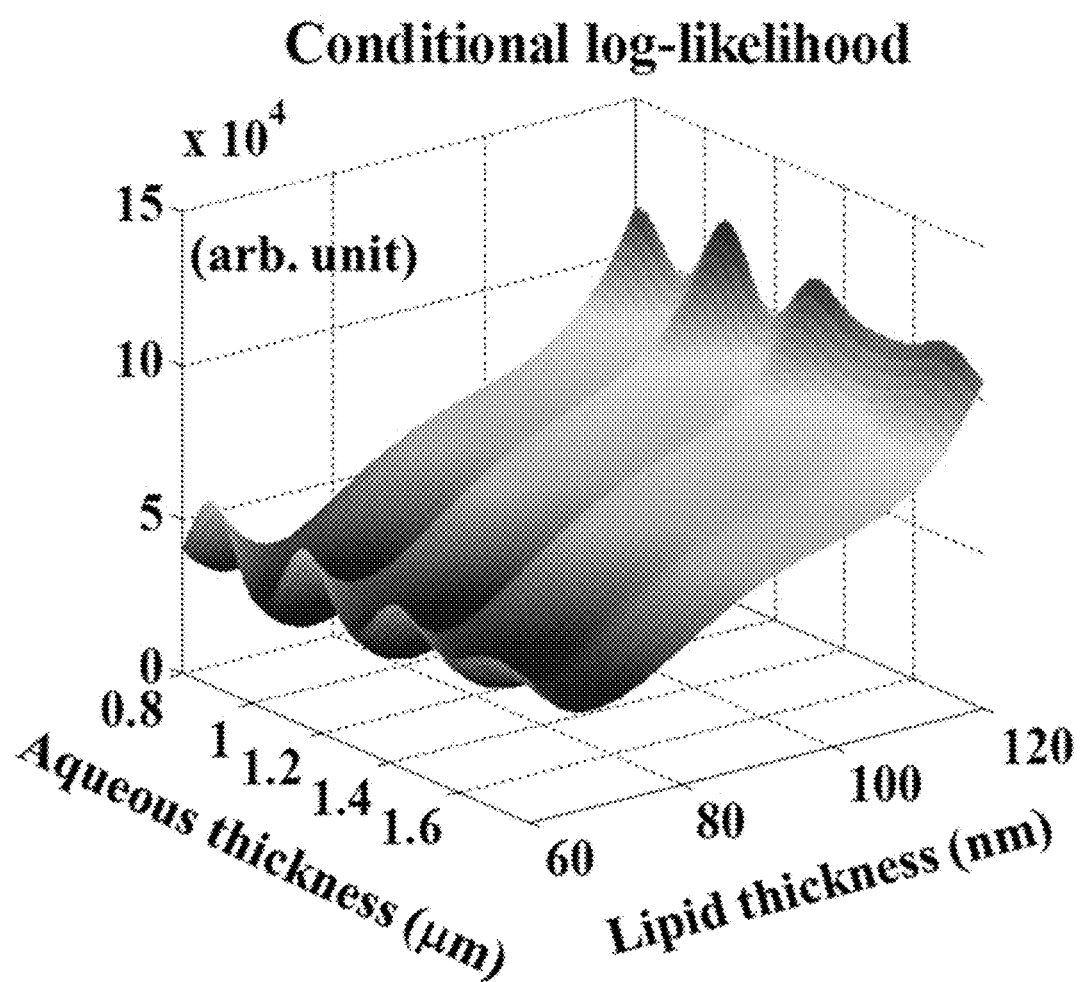
FIG. 5(a) graphically illustrates a conditional log-likelihood that one measured spectrum is generated by different lipid and aqueous thicknesses.
Figure 5B:
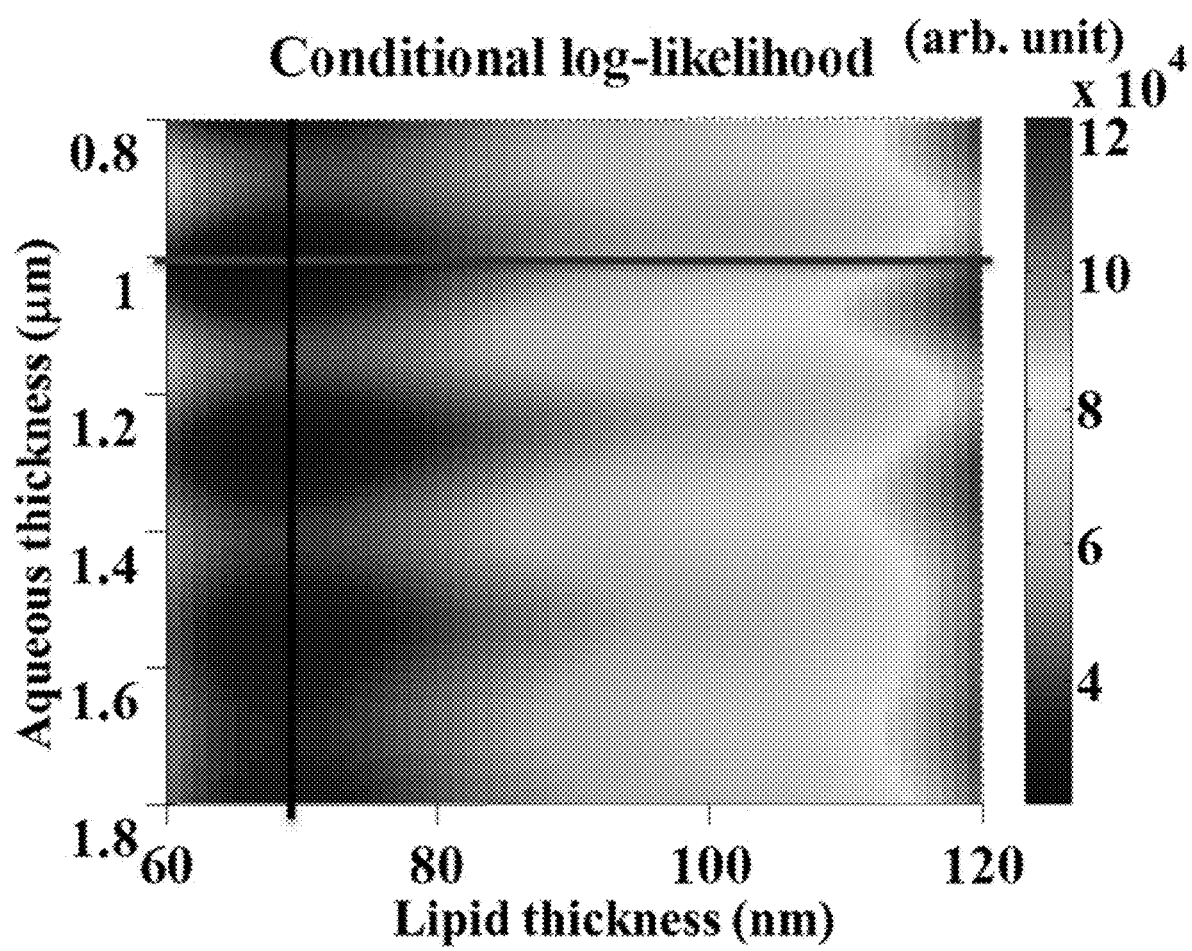
FIG. 5(b) is a top view of the conditional log-likelihood of FIG. 5(a).
Figure 5C:
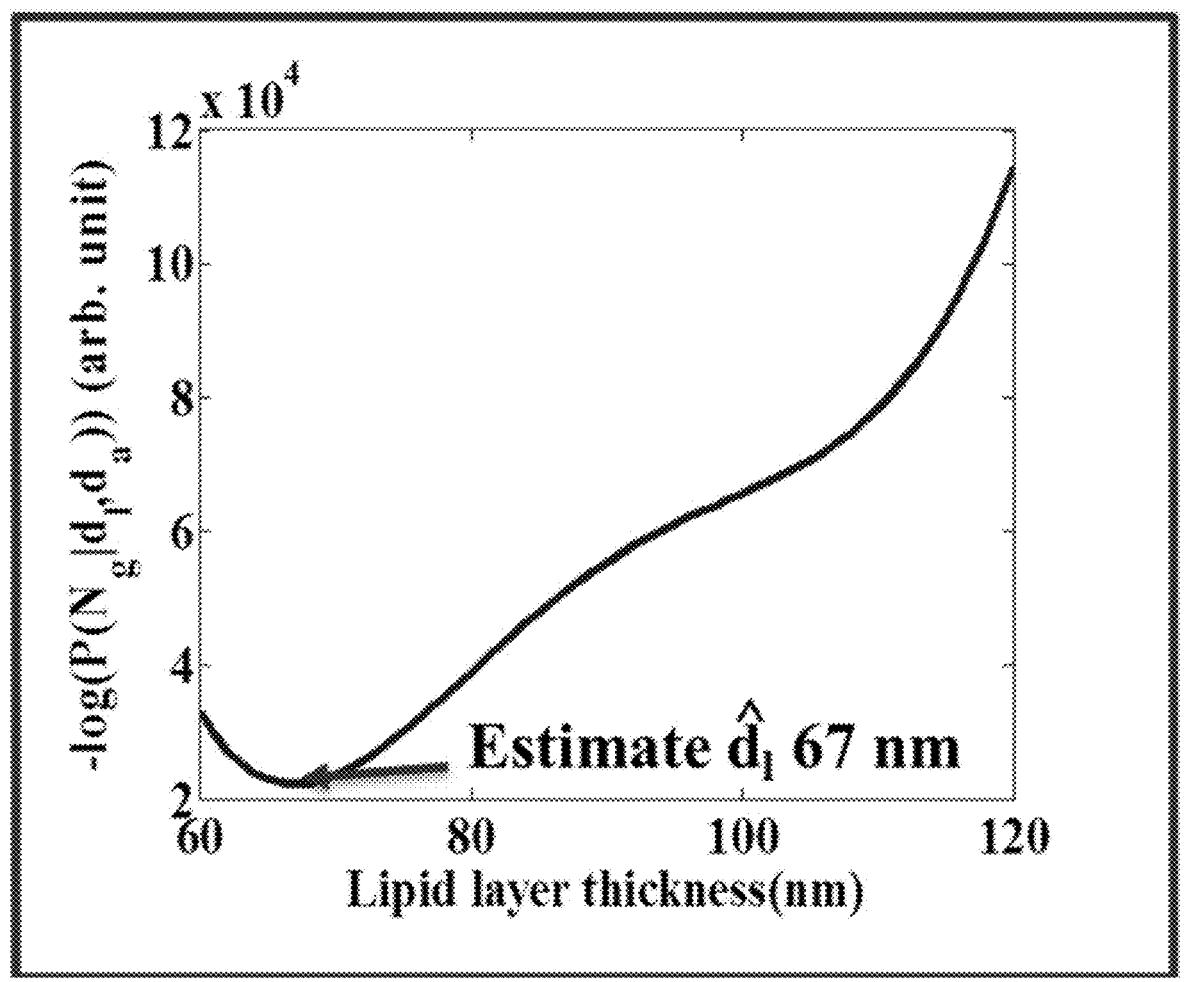
FIG. 5(c) is a conditional log-likelihood along the horizontal line in FIG. 5(b) and the lipid layer thickness estimate.
Figure 5D:
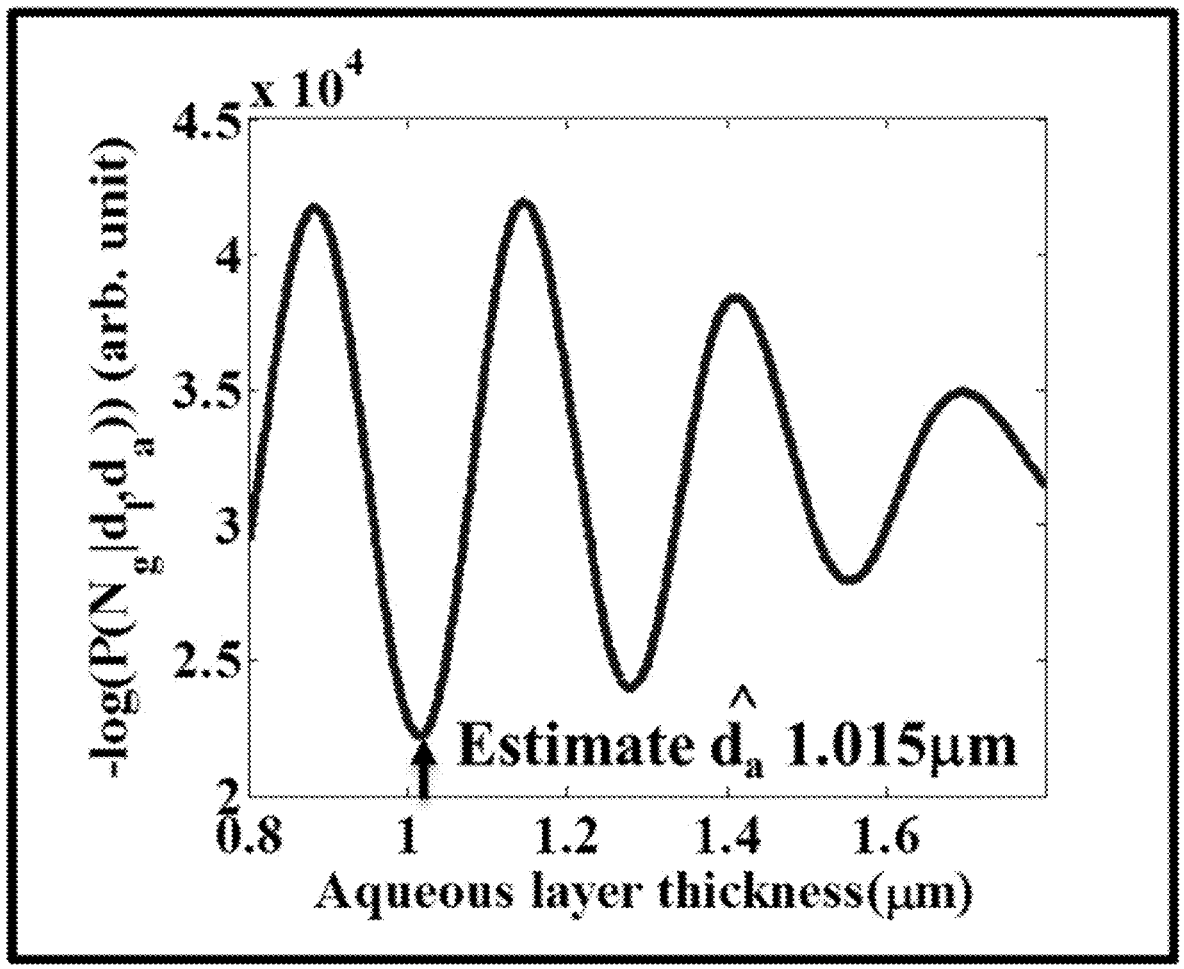
FIG. 5(d) is a conditional log-likelihood along the vertical line in FIG. 5(b) and the aqueous layer thickness estimate.

For the experimental application of the non-limiting embodiment of an SDT-OCT approach described above, we first conducted measurements at a single point on the phantom. The phantom was accurately positioned in the sample arm using optical length match between the reference and sample arms. The reference arm was then blocked for the rest of the experiment, while using the air-phantom interface as reference to minimize the effects of environmental vibrations. The exposure time was set to be the limit imposed by the line-camera of 20 µs. The measured spectrum (an array with 8192 elements) was captured at the center of the phantom and used as the input to the ML estimator. FIG. 5(a) shows the simultaneous estimation of thicknesses for both layers using the ML estimator. In FIG. 5(a), the false color represents the negative conditional log-likelihood that one measured spectrum is generated by different possible lipid and aqueous layer thicknesses. FIG. 5(b) is the top view of the conditional-log likelihood shown in FIG. 5(a), where the horizontal axis and the vertical axis represent sets of lipid layer thickness and aqueous layer thickness, respectively. The dual estimates are determined by the coordinates of the minimum value. FIGS. 5(c) and 5(d) show the profile of the log-likelihood of the two lines passing across the minimum in FIG. 5(b). The estimates were found to be 67 nm and 1.015 µm for the lipid and aqueous layers, respectively. To quantify the repeatability and robustness of the estimator, we repeated the measurements 2000 times at the center point of the phantom. The measured thicknesses were found to be 66.8±0.8 nm and 1012.3±3.7 nm, respectively, which is within the uncertainty boundaries given by the ground truth. Results show that the ML estimator is robust and achieves nanometer precision, as was predicted in for the single layer sample and now extended to two layers.

It is noteworthy that the lipid layer thickness estimates are more precise compared to those of the aqueous layer. The reason for this difference is that the refractive index change in the lipid layer phantom is larger compared to that of the aqueous layer phantom. The greater the refractive index change, the stronger is the layer interface, yielding more precise measurement of the thickness estimation task.

2.5 Thickness Maps Measurement

Figure 6A:
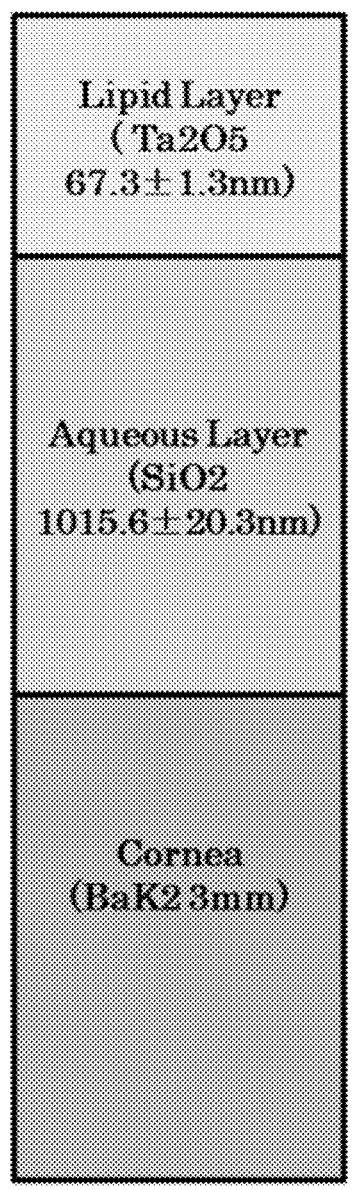
FIG. 6(a) schematically illustrates structure of a two-layer phantom.
Figure 6B:
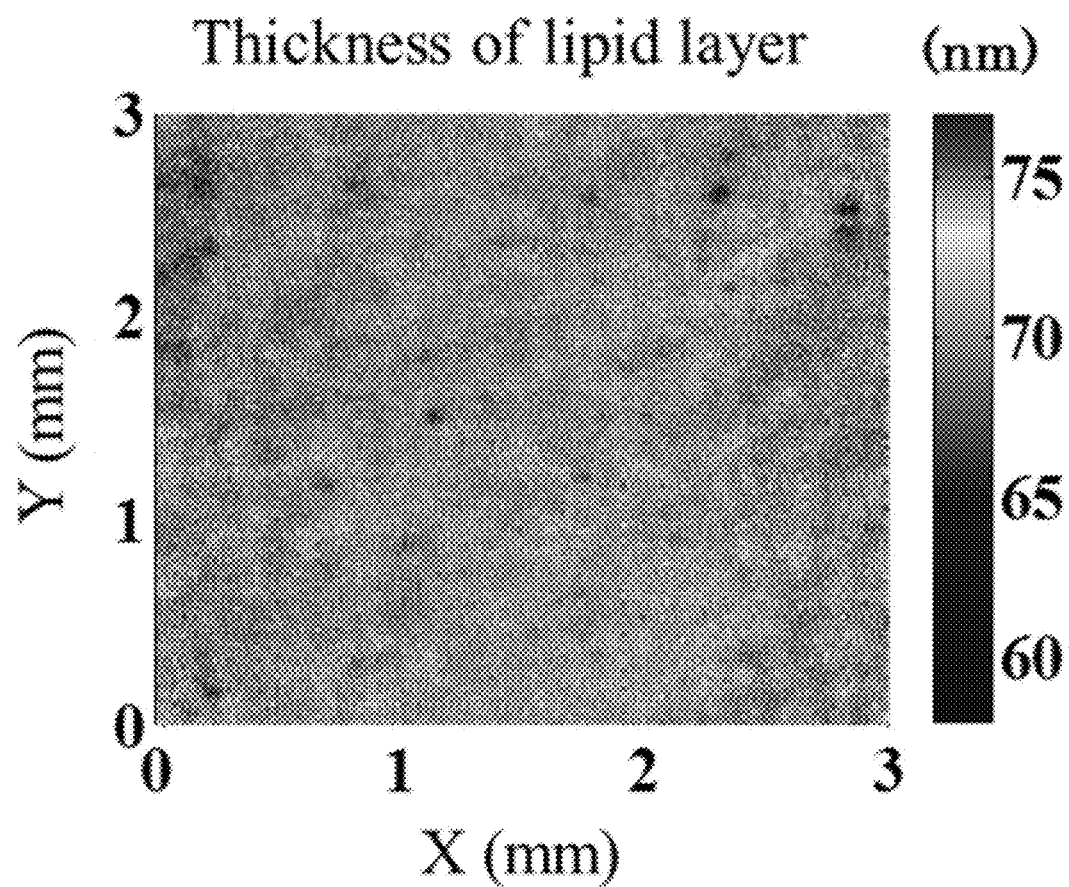
FIG. 6(b) is a thickness map of the lipid layer of the two-layer phantom of FIG. 6(a).
Figure 6C:
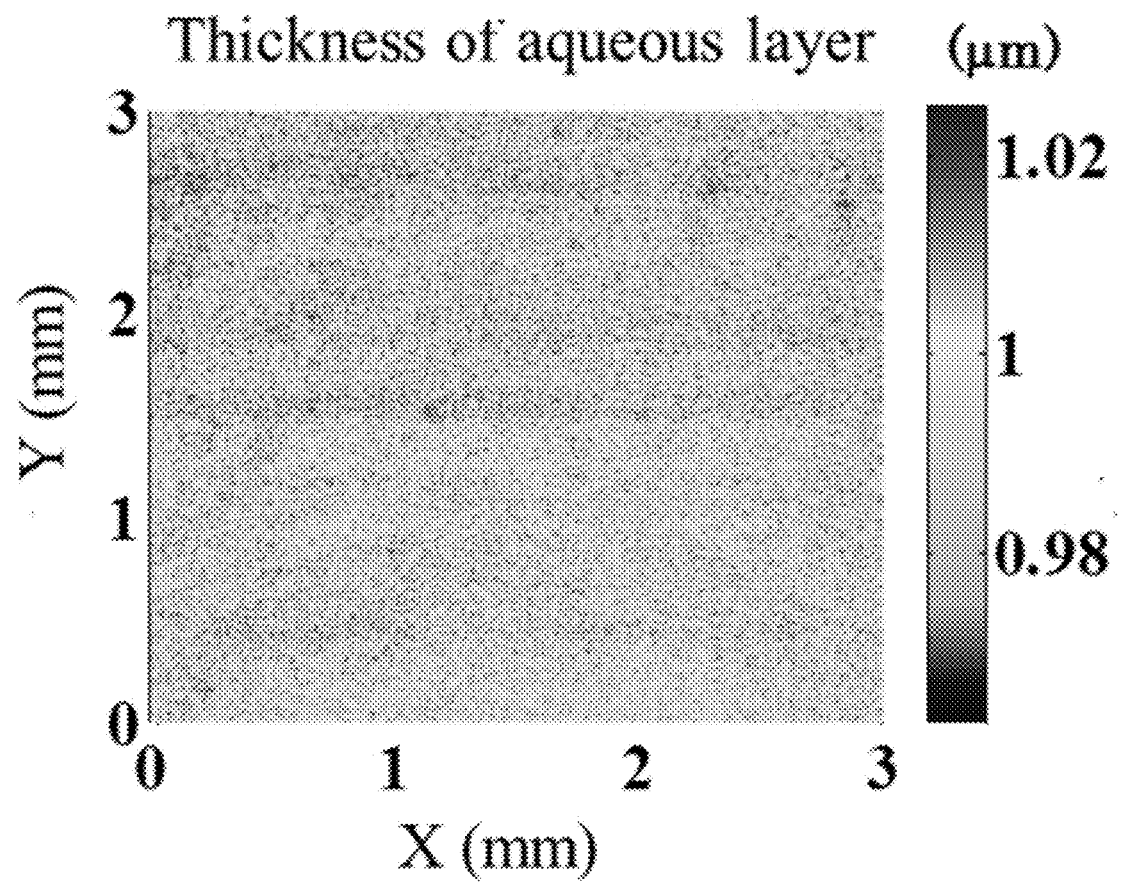
FIG. 6(c) is a thickness map of the aqueous layer of the two-layer phantom of FIG. 6(a).
Figure 6D:
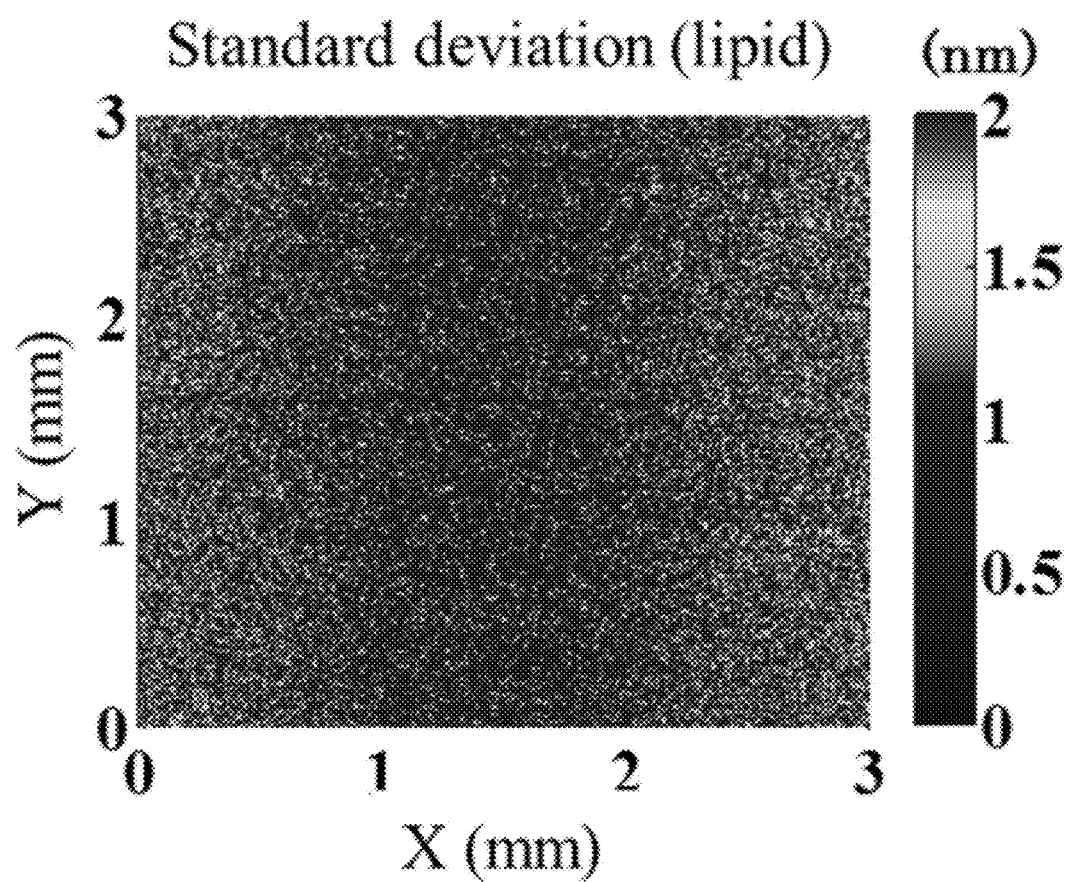
FIG. 6(d) is a repeatability distribution for the lipid layer of the two-layer phantom of FIG. 6(a).
Figure 6E:
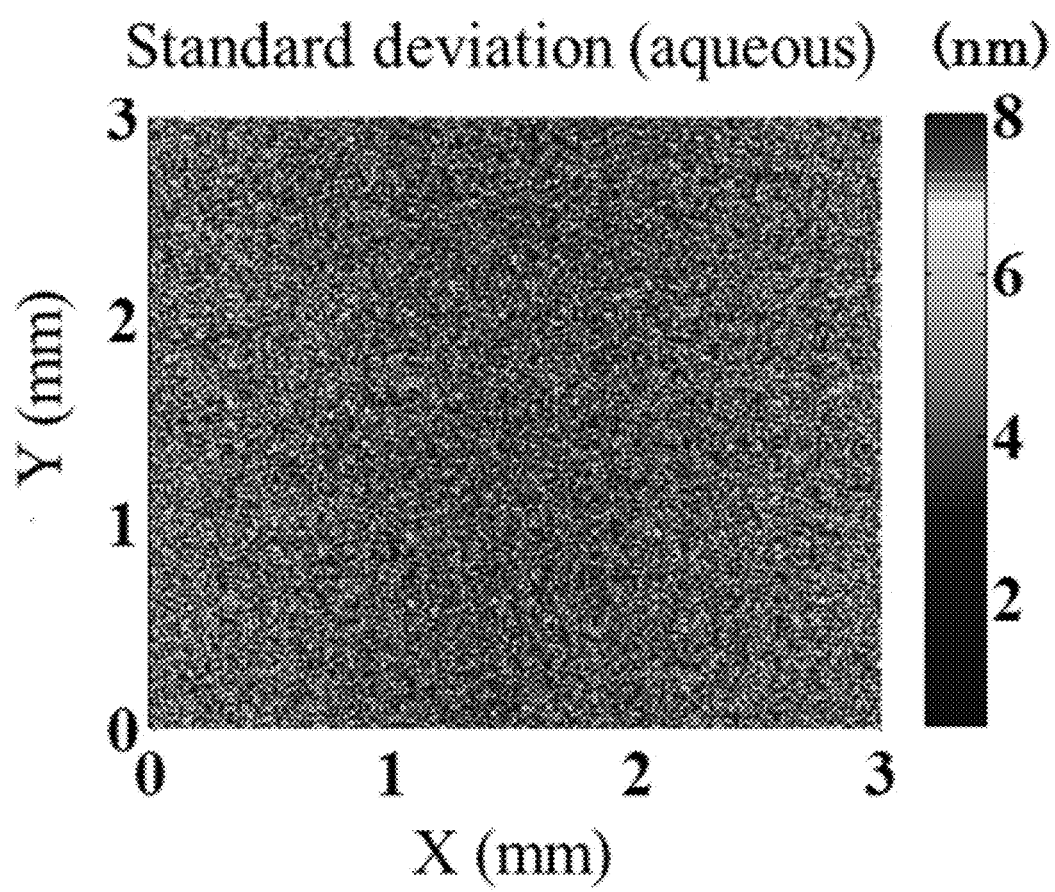
FIG. 6(e) is a repeatability distribution for the aqueous layer of the two-layer phantom of FIG. 6(a).

After validating the ML estimator at a single point, we applied a telecentric scanning on the phantom to get the associated 2D thickness maps. Data were acquired in a 3 mm by 3 mm area with 300 by 300 sampling points (see FIGS. 6(b) and (c)). To make maximum use of the 20 µm lateral PSF of the system, the data points were acquired with 10 µm sampling step. FIG. 6(a) shows the structure of the phantom. The measured thickness maps are shown in FIGS. 6(b) and (c). The mean thicknesses of the measurements across the imaged area are 67.7 nm and 1006.0 nm for the lipid layer and aqueous layer, respectively, which are consistent with the values set by the manufacturing process. To test the repeatability of the measurements on different locations of the phantom, we repeated the measurements of thickness maps five times. The standard deviation distribution of the measurements are shown in FIGS. 6(d) and (e), which shows that the repeatability of the ML estimator is invariant as we scan over the sample.

The acquisition time for each A-scan was 26 µs (i.e. integration time and readout time combined), which is the limit of the line period of the camera, yielding 2.34 seconds for acquiring the thickness maps shown in FIGS. 6(b) and (c). In the case of the tear film thickness estimation, less dense samplings in order to operate at higher speed will be investigated. Provided the tradeoff between imaging speed and the lateral sampling step, as an example, 27 thickness maps per second can be acquired when sampling a 3 mm by 3 mm area with a 80 µm sampling step, yielding video rate recording of the tear film dynamics.

3. Discussion

3.1 Impact of Uncertainties of Refractive Indices

In the example of an SDT-OCT framework described above, we accounted for all sources of noise in the imaging chain. It is worth noting that in OCT, the refractive index and the physical thickness are coupled by a product that is the optical path length (OPL). Thus in estimating thickness from OCT measurements, we also need to account for the uncertainties in index of refraction of the materials. For a given uncertainty of Δn in the refractive index, the uncertainty to the thickness estimation is given as $$\Delta d = \frac{OPL}{n^2}\Delta n. \quad (9)$$

Equation (9) is used to evaluate the impact of the refractive index uncertainties. For the lipid layer of the phantom, the OPL is on the order of 100 nm and the refractive index uncertainty is 0.00005, yielding an uncertainty in thickness estimation due to refractive index in the order of 0.001 nm. For the aqueous layer of the phantom, which has an OPL in the order of microns and a refractive index uncertainty of 0.00005, the uncertainty in thickness estimation due to refractive index is in the order of 0.01 nm. However, as shown in Table 1, the uncertainties of the tear film refractive indices are greater than those of the materials used in the phantom. The impacts on the thickness estimation, due to the uncertainties of refractive index of tear film components, are evaluated to be in the order of 0.01 nm and 1 nm for the lipid layer and aqueous layer, respectively. This investigation shows that the uncertainty in thickness estimation due to refractive index is within the precision of the system.

3.2 Performance Across the Tear Film Thickness Range

Figure 7A:
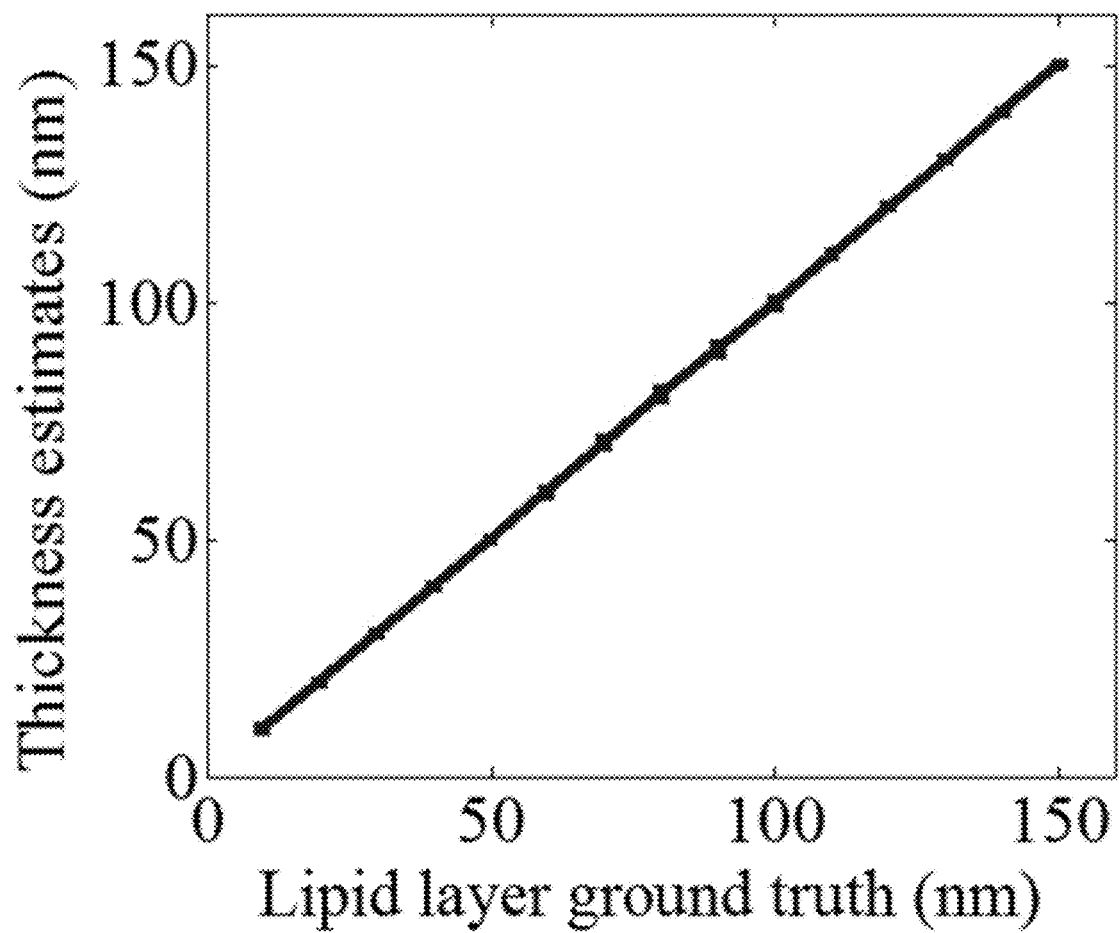
FIG. 7(a) graphically illustrates an estimation accuracy and precision for different thicknesses of a lipid layer.
Figure 7B:
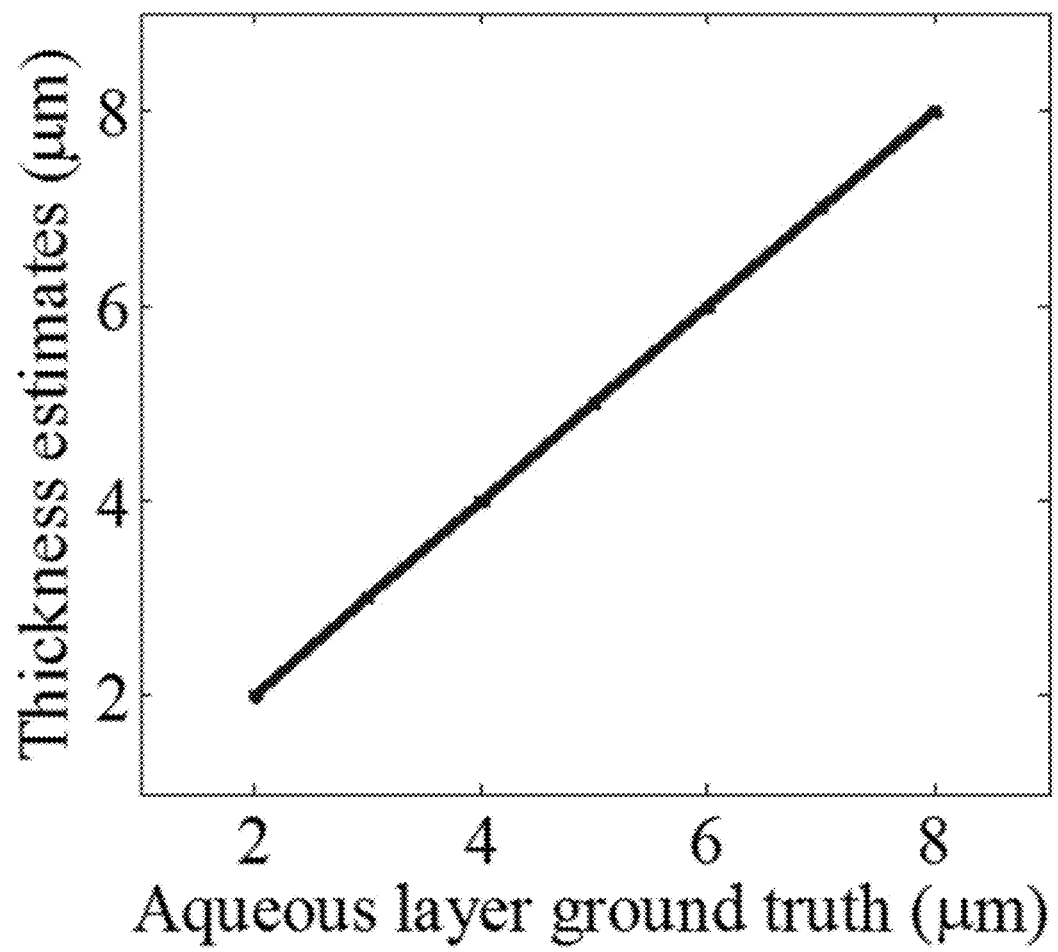
FIG. 7(b) graphically illustrates an estimation accuracy and precision for different thicknesses of an aqueous layer.

In the context of tear film thickness estimation, the thickness of the lipid layer ranges from 20 nm to 150 nm, while the thickness of the aqueous layer is in the order of microns. To investigate the performance of the ML estimator across such thickness ranges, we adopted a simulation approach, in which we could set the ground truth of the lipid and aqueous layer thicknesses. In the simulation, we also took into account the roughness interface between the aqueous layer and the corneal surface, which has been studied to be 129 nm in terms of the standard deviation of the surface height. For a given ground truth of tear film thicknesses, the mean and the variance of the output spectra from the OCT system were simulated using Eq. (5) and Eq. (8), respectively. The mean and the variance of the spectra were then input to a Gaussian random number generator, which represented the normal distribution in Eq. (4), to generate one instance of the simulated spectra. The simulated spectrum was then input to the ML estimator, from which the output were thicknesses estimates. For each given ground truth, 2000 simulated spectra were generated to evaluate the RMSE of the estimates. The ground truth of thicknesses were then varied to investigate the performance of the ML estimator across the tear film thickness range. Results are shown in FIG. 7, which show that ML is an unbiased estimator with precision <5 nm for the lipid layer and <20 nm for the aqueous layer.

3.3 Processing Speed

The bottleneck of the current work is the post processing time. At this time, all the post processing is done with MATLAB®, and it takes about 10 hours to calculate the thickness maps shown in FIGS. 6(b) and 6(c). The intensive computational task is to calculate the conditional log-likelihood distribution. Although we leveraged the parallel computing toolbox, the CPU computing is fundamentally limited by the number of cores available. In other embodiments, other GPU framework may be leveraged to significantly speed up the post processing time and allow for real time visualization of thickness maps.

Measurement of Multi-Layer Repeating Structures

The preceding sections have described the measurement of a multi-layer structure in the context of the lipid and aqueous layers of a tear film. However, these techniques are not limited to use with tear films, and can be applied to other multi-layer structures such as industrial coatings (films, tapes, etc.), biomedical samples (skin tissue, corneal tissue, etc.), and other multi-layer constructs.

Figure 8:
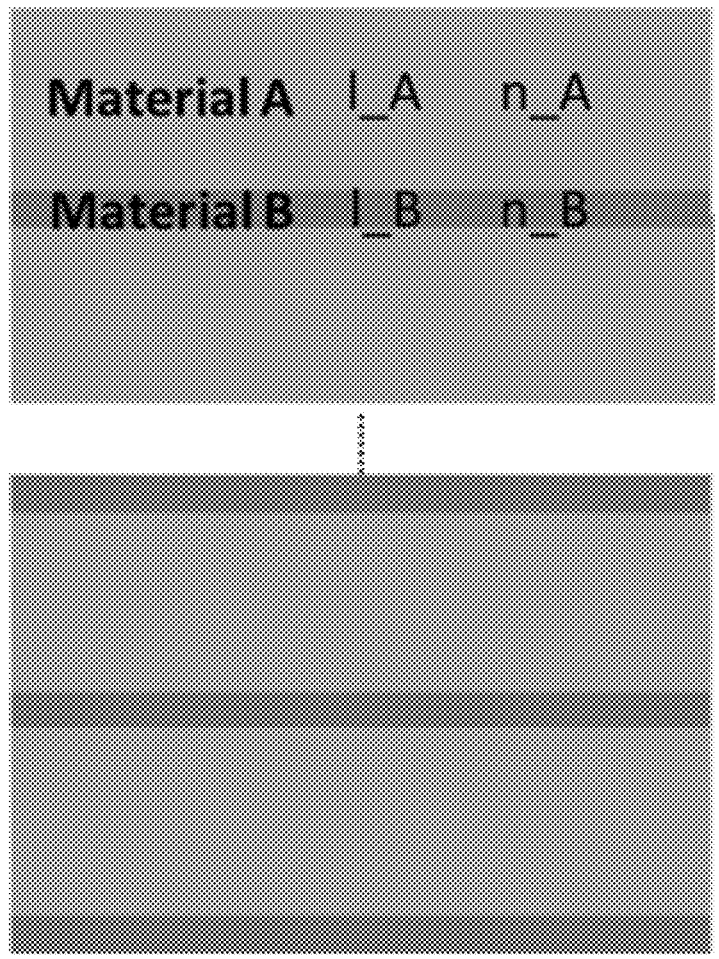
FIG. 8 is a schematic representation of a multi-layer structure with repeating layers.

FIG. 8 schematically shows a multi-layer structure including an alternating series of layers of two materials, including a layer of material A, having a thickness "l_A" and a refractive index of "n_A," and a layer of material B, having a thickness "l_B" and a refractive index of "n_B." Materials A and B may be any desired materials having at least some degree of reflectance and transmission in the spectral window of the OCT system. In one example, the multi-layer structure is a skin stratum corneum layer structure, which is a multi-stack of corneocytes and intercellular lipids, where one stack unit includes at least a first layer and a second layer.

The example of a multi-layer sample in FIG. 8 consists of repeating stack units of two different materials A and B. This type of multi-layer structure can be found in different industrial films, such as coatings and tapes, in biomedical samples, such as specific skin or corneal tissue layers, and in other structures. For the quality control of developing the industrial films or the biopsy of biomedical samples, it is often desirable to know or estimate the number of stacks and the thicknesses of different material components.

Figure 9:
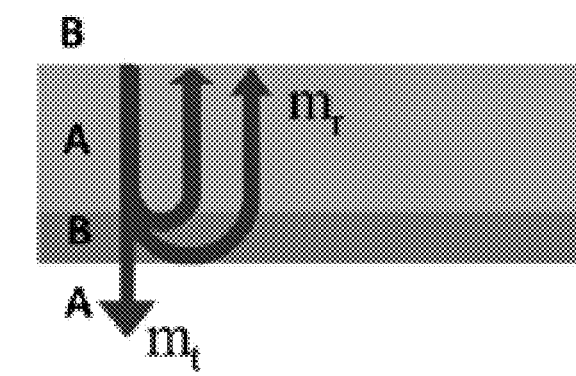
FIG. 9 illustrates different reflection and transmission scenarios for three stack units, depending on their location in the stack.
Figure 9:
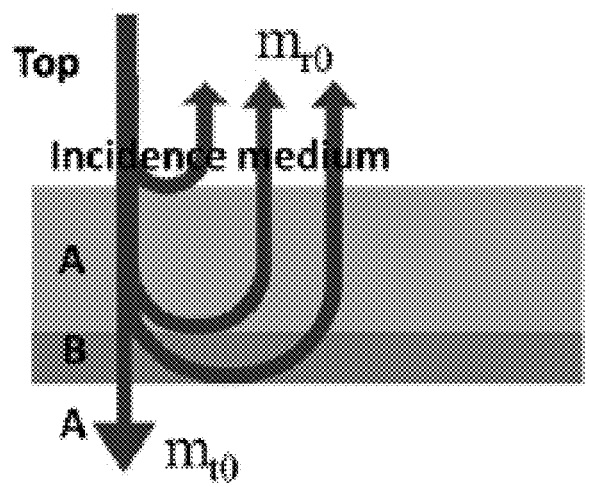
Figure 9:
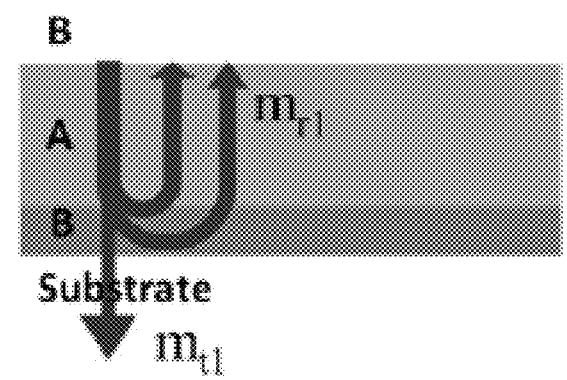

To mathematically model the multi-layer structure of FIG. 8, a stack that consists of one layer of A and one layer of B is considered as a basic stack unit and three scenarios are taken into account: the stack unit lies on the top, the middle, and the bottom of the sample, as shown in FIG. 9. It is assumed that the various stack units have the same A-B structure and the light beam from the OCT hardware has a normal incidence on the multi-layer sample; however, our techniques may also be applied to multi-layer structures that do not necessarily have the same repeating A-B structure and in situations where the light beam is incident at other angles to the sample.

For the stack unit that lies in the middle of the multi-layer structure, the reflected optical response can be derived as:

$$m_r(\omega) = r_{AB} \exp(i2n_A l_A k) = r_{BA}(1 - r_{BA}^2)\text{EXP}(i2n_A l_A k + i2n_B l_B k) \quad (10)$$

where $n_A$ and $n_B$ are the refractive indices of materials A and B; $l_A$ and $l_B$ are the thicknesses of layers A and B; k is the wavenumber; $r_{AB}$, $r_{BA}$ are the reflection coefficients of the field amplitude at the A-B and B-A interfaces, which can be written as:

$$r_{AB} = \frac{n_A - n_B}{n_A + n_B} \quad (11)$$

$$r_{BA} = \frac{n_B - n_A}{n_B + n_A} \quad (12)$$

The transmitted optical response can be written as:

$$m_t(\omega) = t_{AB} t_{BA} \exp(in_A l_A k + in_B l_B k) \quad (13)$$

where $t_{AB}$ and $t_{BA}$ are the transmission coefficients of the field amplitude at the A-B and B-A interfaces and are given as:

$$t_{AB} = 1 + r_{AB} \quad (14)$$

$$t_{BA} = 1 + r_{BA} \quad (15)$$

For the stack unit that is on the top end of the sample and is in contact with the incidence medium, the reflected and transmitted optical response can be derived as:

$$m_t(\omega) = t_{AB} t_{BA} \exp(i n_A l_A k + i n_B l_B k) \tag{16}$$

$$m_{t0}(\omega) = t_{iA} m_t(\omega) \tag{17}$$

If a rough interface between the sample and the incidence medium presents and the surface height of that interface has a root mean square value of $\sigma_0$, the reflection and transmission coefficients of the field amplitude can be then written as:

$$r_{iA} = \frac{n_i - n_A}{n_i + n_A} \exp(-2 n_i^2 k^2 \sigma_0^2) \tag{18}$$

$$t_{iA} = \frac{2 n_A}{n_i + n_A} \exp\left(-\frac{1}{2}(n_i - n_A)^2 k^2 \sigma_0^2\right) \tag{19}$$

$$t_{Ai} = \frac{2 n_i}{n_i + n_A} \exp\left(-\frac{1}{2}(n_i - n_A)^2 k^2 \sigma_0^2\right). \tag{20}$$

in which $n_i$ is the refractive index of the incidence medium.

For the stack unit on the bottom end of the sample, which may be in contact with a substrate, the reflected optical response can be written as:

$$m_{r1}(\omega) = r_{AB} \exp(i 2 n_A l_A k) + r_{Bs}(1 - r_{BA}^2) \exp(i 2 n_A l_A k + i 2 n_B l_B k) \tag{21}$$

in which $r_{Bs}$ is the reflection coefficient of the field amplitude at the interface between layer B and the substrate. If a rough interface presents and the surface height has a root mean square value of $\sigma_1$, the reflection coefficient can be written as:

$$r_{Bs} = \frac{n_B - n_s}{n_B + n_s} \exp(-2 n_B^2 k^2 \sigma_1^2). \tag{22}$$

where $n_s$ is the refractive index of the substrate.

For a given sample that has a total number of Z stack units of A and B, the total optical response from the multi-layer sample can be written as:

$$m(\omega) = m_{r0}(\omega) + m_{t0}(\omega) \sum_{j=1}^{Z-2} m_r(\omega)(m_t(\omega))^{2j-1} t_{Ai} + m_{t0}(\omega)(m_t(\omega))^{2Z-3} t_{Ai} m_{r1}(\omega) \tag{23}$$

Taking into account the statistical noise of the optical source, Poisson noise, and dark noise of the detector, the expected ensemble mean of the acquired spectra for a given sample is given as:

$$\langle\langle\langle N_g(x, \Delta t)\rangle\rangle\rangle = \frac{R(x)}{e} \Delta t \int_{\omega_x - \Delta \omega_x}^{\omega_x} S(\omega) |m(\omega)|^2 d\omega + N_{dark}. \tag{24}$$

where $S(\omega)$ is the power spectral density of the source, $N_{dark}$ is the average dark noise over the integration time, $\Delta \omega$ is the optical frequency bandwidth at the $x^{th}$ pixel, e is the charge of an electron, and $R(x)$ is the pixel's responsivity.

The conditional probability of observing one spectrum $N_g(x, \Delta t)$ for a given stack number and layer thicknesses are given as:

$$P(N_g(x, \Delta t) | Z, l_A, l_B) = \frac{1}{(2\pi)^{\frac{M}{2}} \prod_x [K_{N_g}(x, \Delta t)]^{\frac{1}{2}}} \times \exp\left[-\frac{1}{2} \sum_x \frac{(N_g(x, \Delta t) - \langle\langle\langle N_g(x, \Delta t)\rangle\rangle\rangle)^2}{K_{N_g}(x, \Delta t)}\right]. \tag{25}$$

in which M is the number of pixels and $K_{N_g}$ is the variance and has been derived as described earlier in this patent. Based on the principle of the maximum-likelihood estimation, the estimates for a measured spectrum $N_g(x, \Delta t)$ are given as:

$$(\hat{l}_A, \hat{l}_B, \hat{Z}) = \underset{l_A, l_B, Z}{\arg \min}(-\log(P(N_g(x, \Delta t) | l_A, l_B, Z))) \tag{26}$$

If the roughness of the top and bottom interfaces are unknown, they can be treated as parameters to be estimated and the corresponding estimates are expressed as:

$$(\hat{l}_A, \hat{l}_B, \hat{Z}, \hat{\sigma}_0, \hat{\sigma}_1) = \underset{l_A, l_B, Z, \sigma_0, \sigma_1}{\arg \min}(-\log(P(N_g(x, \Delta t) | l_A, l_B, Z, \sigma_0, \sigma_1))) \tag{27}$$

\*\*\*

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims. The claims can encompass embodiments in hardware, software, or a combination thereof.

The invention claimed is:

1. A system for determining layer thicknesses of a multi-layer structure, the system comprising:
   a low coherence interferometry component configured to generate data about the multi-layer structure based on a detected spectral interference pattern spectrum, the low coherence interferometry component comprising a broadband light source, a beam splitter, a reference arm, a sample arm, and a spectrometer; and
   a statistical estimator component configured to generate an estimate of a first layer thickness of the multi-layer structure and an estimate of a second layer thickness of the multi-layer structure based on the generated data from the detected spectral interference pattern spectrum and based on data on broadband light source noise and spectrometer noise, wherein the statistical estimator component determines the estimate of the first layer thickness and the estimate of the second layer thickness based on a statistical likelihood of the detected spectral interference pattern spectrum being generated by the estimated first and second layer thicknesses out of different possible combinations of potential first and second layer thicknesses; and wherein the statistical estimator component generates the estimates of the first and second layer thicknesses at a higher resolution than an axial resolution of the low coherence interferometry component;

wherein the multi-layer structure comprises a plurality of stack units, the stack units each including a first layer of a first material on top of a second layer of a second, different material, the first layer corresponding to the first layer thickness and the second layer corresponding to the second layer thickness;

wherein the statistical estimator component is configured to further determine an estimate for a number of stack units in the multi-layer structure based on the inputted spectrum array;

wherein the plurality of stack units comprises: (i) a top stack unit including at least a layer of the first material and a layer of the second material, the layer of the first material of the top stack unit adjacent an incidence medium; (ii) a bottom stack unit including at least a layer of the first material and a layer of the second material, the layer of the second material of the bottom stack unit adjacent a substrate; and (iii) at least one middle stack unit including at least a layer of the first material and a layer of the second material;

wherein the spectrometer is configured to collect light reflected or scattered back from the top stack unit, light reflected or scattered back from the bottom stack unit, and light reflected or scattered back from the at least one middle stack unit.

2. The system of claim 1, wherein the statistical estimator component is configured to further determine an estimate for a roughness of at least one of a top interface and a bottom interface of the stack units.

3. The system of claim 1, wherein the statistical estimator component is at least one of a maximum-likelihood estimator, a maximum posteriori estimator, or a posterior mean estimator.

4. The system of claim 1, wherein the low coherence interferometry component is a micron axial resolution low coherence intereferometry component and wherein the statistical estimator component is a nanometer resolution statistical estimator.

5. A system for determining layer thicknesses of a multi-layer structure, the system comprising:

a low coherence interferometry component configured to generate data about the multi-layer structure based on a detected spectral interference pattern spectrum, the low coherence interferometry component comprising a broadband light source, a beam splitter, a reference arm, a sample arm, and a spectrometer; and a statistical estimator component configured to generate an estimate of a first layer thickness of the multi-layer structure and an estimate of a second layer thickness of the multi-layer structure based on the generated data from the detected spectral interference pattern spectrum and based on data on broadband light source noise and spectrometer noise, wherein the statistical estimator component determines the estimate of the first layer thickness and the estimate of the second layer thickness based on a statistical likelihood of the detected spectral interference pattern spectrum being generated by the estimated first and second layer thicknesses out of different possible combinations of potential first and second layer thicknesses; and wherein the statistical estimator component generates the estimates of the first and second layer thicknesses at a higher resolution than an axial resolution of the low coherence interferometry component;

wherein the low coherence interferometry component comprises an operational bandwidth of at least 200 nm;

wherein the low coherence interferometry component operates in a spectral window including 600 nm and 1000 nm wavelengths.

6. The system of claim 5, wherein the low coherence interferometry component comprises an operational bandwidth of approximately 400 nm.

7. The system of claim 1, wherein the broadband light source noise data comprises a quantified intensity noise of the broadband light source, and wherein the spectrometer noise data comprises a quantified Poisson noise of the spectrometer and a quantified dark noise of the spectrometer.

8. The system of claim 1, wherein the statistical estimator component is configured to simultaneously generate the estimate of the layer thicknesses based on the generated data, the broadband light source noise data, and the spectrometer noise data.

* * * * *